(12) United States Patent
Steffens et al.

(10) Patent No.: US 8,999,699 B2
(45) Date of Patent: Apr. 7, 2015

(54) XYLANASES ACTIVE DURING PRETREATMENT OF CELLULOSIC BIOMASS

(75) Inventors: John Steffens, Chapel Hill, NC (US); Paul Oeller, Research Triangle Park, NC (US); Yoshimi Barron, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/821,889

(22) PCT Filed: Sep. 8, 2011

(86) PCT No.: PCT/US2011/050846
§ 371 (c)(1),
(2), (4) Date: Jun. 27, 2013

(87) PCT Pub. No.: WO2012/033926
PCT Pub. Date: Mar. 15, 2012

(65) Prior Publication Data
US 2013/0273611 A1    Oct. 17, 2013

Related U.S. Application Data

(60) Provisional application No. 61/381,455, filed on Sep. 10, 2010.

(51) Int. Cl.
*C12N 1/20* (2006.01)
*C12P 19/14* (2006.01)
*C12N 9/24* (2006.01)
*C12P 7/14* (2006.01)

(52) U.S. Cl.
CPC ............ *C12P 19/14* (2013.01); *C12N 9/248* (2013.01); *C12N 9/2482* (2013.01); *C12P 7/14* (2013.01); *C12P 2201/00* (2013.01)

(58) Field of Classification Search
USPC ............................................. 435/163, 320.1
See application file for complete search history.

(56) References Cited

U.S. PATENT DOCUMENTS

| | | |
|---|---|---|
| 7,314,974 B2 * | 1/2008 | Cao et al. ................ 800/289 |
| 2003/0233675 A1 | 12/2003 | Cao et al. |
| 2008/0121359 A1 | 5/2008 | Holtzapple et al. |
| 2009/0004706 A1 | 1/2009 | Vandeberg et al. |
| 2009/0155238 A1 | 6/2009 | Weiner et al. |

OTHER PUBLICATIONS

Winterhalter et. al., UniProt Database, Accession No. Q60037, Nov. 1997.*
Feng et al., Geneseq Database, Accession No. AWL91289, May 2009.*
Endo et al., Biochemistry, 40, 914-919, 2001.*
Sajjad et al., J. Biotechnol., Jan. 1, 2010;145(1):38042, abstract only.*
Wikapedia website, Aug. 2014, "Start codon".*
International Search Report, International Application No. PCT/US11/050846, completion date: Dec. 29, 2011.

* cited by examiner

*Primary Examiner* — Maryam Monshipouri
(74) *Attorney, Agent, or Firm* — Dale Skalla

(57) ABSTRACT

Compositions and methods are provided for treating lignocellulosic material with a xylanase enzyme having xylanase activity. The enzyme is stable and active at increased pHs and temperatures. The present invention therefore provides methods for hydrolyzing lignocellulosic material, especially cellulose and hemicellulose, which are major components of the cell wall of non-woody and woody plants. The methods for hydrolyzing cellulose and hemicellulose can be used on any plant, wood or wood product, wood waste, paper pulp, paper product or paper waste or byproduct.

1 Claim, No Drawings

XYLANASES ACTIVE DURING PRETREATMENT OF CELLULOSIC BIOMASS

CROSS-REFERENCE TO RELATED APPLICATIONS

This application is a 371 of International Application No. PCT/US2011/050846 filed Sep. 8, 2011, which claims priority to U.S. Provisional Application No. 61/381,455 filed Sep. 10, 2010, the contents of which are incorporated herein by reference.

REFERENCE TO SEQUENCE LISTING SUBMITTED ELECTRONICALLY

An official copy of a Sequence Listing submitted electronically via EFS-Web as an ASCII-formatted Sequence Listing with a file named "72840SequenceListing.txt," created on Jul. 1, 2010, having a size of 76 kb and filed concurrently with the Specification is a part hereof and is herein incorporated by reference as if set forth in its entirety.

FIELD OF THE INVENTION

The present invention relates generally to methods of using enzymes having xylanase activity to process lignocellulosic materials.

BACKGROUND OF THE INVENTION

Hemicelluloses are a group of plant-derived heteropolysaccharides, which are associated with cellulose and lignin. The most common hemicelluloses are xylan, glucuronoxylan, arabinoxylan, glucomannan and xyloglucan.

Xylanases catalyze endohydrolysis of the 1,4-β backbone of xylan, a heteropolymer of xylose. Xylanases are naturally produced by organisms such as algae, bacteria, fungi, gastropods and protozoa, which can use xylose as a carbon source for cellular metabolism. See, Prade (1995) *Biotech. Genet. Eng. Rev.* 13:100-131.

Commercial applications of xylanases in the feed, food/beverage and technical industries (e.g., biomass applications) vary. In the feed industry, xylanases are used in monogastric and ruminant feeds to increase digestibility and nutritive value of poorly degradable feeds (e.g., barley, silage and wheat). In the food/beverage industry, xylanases are used in fruit and vegetable processing to make nectars, purees and juices, in brewing and winemaking to hydrolyze mucilaginous substances in grains for fermentation, and in baking to improve dough quality (e.g., elasticity and strength). In the technical industry, xylanases are used in papermaking to reduce chlorine consumption and toxic discharge during bleaching of wood pulp, in textile processing to reduce or replace chemical retting, and in bioremediation/bioconversion to treat/recycle wastes and to produce biofuels and fine chemicals.

In many of these applications, xylanases are used in connection with various other lignocellulolytic enzymes such as cellulases, hemicellulases, ligninases, pectinases and proteases. Lignocellulolytic enzymes therefore have significant potential applications in the feed, food/beverage and technical industries. New compositions and methods for efficiently processing lignocellulosic materials are needed.

BRIEF SUMMARY OF THE INVENTION

Compositions and methods are provided for processing lignocellulosic materials. The compositions include at least one enzyme wherein the enzyme has xylanase activity and wherein the enzyme is active at a high temperature and a high pH. Xylanase enzymes include xylanases, particularly family 10 xylanases, that are thermotolerant and alkaliphilic. Because of the alkaliphilic nature of the enzymes, they can be prepared as compositions or formulations which are further incorporated into processes that are performed at a high pH, typically pH 8.5 or higher. The enzymes retain activity at high temperatures. The compositions can also include additional enzymes for processing lignocellulosic materials such as cellulases, hemicellulases, ligninases, pectinases and proteases.

The xylanase enzymes of the invention can be used to transform an organism of interest. Such organisms include bacteria, fungi, and plants. Thus, plants, plant parts and seed that have been modified to express at least one of the xylanase enzymes of the invention are disclosed. It is recognized that plants modified to express a xylanase enzyme can display negative agronomic phenotypes which may be ameliorated by selecting a xylanase from the family 10 class of enzymes.

The methods involve the use of the xylanase enzymes or the compositions described herein to hydrolyze xylans in lignocellulosic material in various feed, food/beverage and technical applications. The xylanase enzymes are useful for the bioconversion of lignocellulosic materials into simpler polysaccharides or even monosaccharides. These monosaccharides or polysaccharides can be used, for example, for the production of feed or food/beverages such as a cereal-based animal feed, a wort or beer, a milk or milk product, a fruit or vegetable product; for the production of fine chemicals such as butanol, ethanol, methanol and/or propanol; or for the production of fuels including biofuels such as bioethanol, bioethers, biodiesel and syngas. The xylanase enzyme is useful in the bioconversion of lignocellulosic materials because it is thermostable and can be used at a high pH.

The following embodiments are encompassed by the present invention.

1. A composition comprising at least one xylanase enzyme wherein the composition has a pH of at least about pH 8.5, and wherein said xylanase enzyme is a thermotolerant and alkaliphilic family 10 xylanase.

2. The composition of embodiment 1, wherein said xylanase enzyme has an amino acid sequence selected from the group consisting of:
   a) the amino acid sequence set forth in SEQ ID NOs: 6, 8 or 10;
   b) an amino acid sequence having at least about 90% sequence identity to an amino acid sequence set forth in SEQ ID NOs: 6, 8 or 10;
   c) an amino acid sequence having at least about 95% sequence identity to an amino acid sequence set forth in SEQ ID NOs: 6, 8 or 10;
   d) an amino acid sequence having at least about 99% sequence identity to an amino acid sequence set forth in SEQ ID NOs: 6, 8 or 10; and,
   e) a fragment of SEQ ID NOs: 6, 8 or 10, wherein said fragment retains xylanase activity.

3. The composition of embodiment 1, wherein the composition has a pH of about pH 12.

4. The composition of embodiment 3, wherein the enzyme is stable at temperatures up to about 95° C.

5. The composition of embodiment 1 or 2, further comprising at least one enzyme selected from the group consisting of a cellulase, hemicellulase, ligninase, pectinase and protease.

6. The composition of embodiment 5, wherein the cellulase is selected from the group consisting of a mannan endo-1,4-β-mannosidase, 1,3-β-D-glucan glucanohydrolase, 1,3-β- glucan glucohydrolase, 1,3-1,4-β-D-glucan glucanohydrolase and 1,6-β-D-glucan glucanohydrolase.

7. The composition of embodiment 5, wherein the hemicellulase is selected from the group consisting of an α-L-arabinofuranosidase, α-glucuronidase, acetyl mannan esterase, acetyl xylan esterase, α-galactosidase, β-glucosidase, xylosidase, endo-galactanase, endo-β-1,4-mannanase, endo-α-1,5-arabinanase, exo-β-1,4-mannosidase, exo-β-1,4-xylosidase, feruloyl esterase, ferulic acid esterase, p-cumaric acid esterase, glucuronoxylan xylanohydrolase and xyloglucan endotransglycosylase.

8. The composition of embodiment 5, wherein the ligninase is selected from the group consisting of a diarylpropane peroxidase, glucose oxidase, glyoxal oxidase, lignin peroxidase, manganese peroxidase, methanol oxidase, methanol oxidoreductase, phenol oxidase, phenol peroxidase and veratryl alcohol oxidase.

9. The composition of embodiment 5, wherein the pectinase is selected from the group consisting of a pectolyase, pectozyme and polygalacturonase.

10. The composition of embodiment 5, wherein the protease is selected from the group consisting of an asclepain, bromelain, caricain, chymopapain, collagenase, glycyl endopeptidase, pepsin, pronase, subtilisin and thermolysin.

11. The composition of embodiment 1, 2, or 5, further comprising at least one enzyme selected from the group consisting of an amylase, catalase, cutinase, glucanase, glucoamylase, glucose isomerase, lipase, phytase, pullulanase and xylose isomerase.

12. The composition of embodiment 1, 2, 5, or 11, further comprising at least one agent selected from the group consisting of a chlorine, detergent, hypochlorite, hydrogen peroxide, oxalic acid, peracid, pH-regulating agent, trisodium phosphate, sodium chlorite, sodium nitrate, surfactant, urea and water.

13. The composition of embodiment 1, 2, 5, 11, or 12, further comprising an ethanologenic microorganism such as a bacteria or yeast.

14. A host cell stably transformed with a nucleic acid construct comprising a promoter operably linked to a nucleotide sequence encoding a xylanase enzyme wherein the cell is a bacterial cell, fungal cell, insect cell, mammalian cell or plant cell, wherein the promoter is heterologous with respect to the nucleotide sequence, and wherein the xylanase enzyme is a thermotolerant and alkaliphilic family 10 xylanase.

15. The host cell of embodiment 14 wherein the xylanase enzyme has an amino acid sequence selected from the group consisting of SEQ ID NOs: 6, 8 or 10, or an active variant or fragment thereof.

16. The host cell of embodiment 14, wherein the nucleotide sequence is selected from the group consisting of SEQ ID NOs: 5, 7 and 9.

17. A method of processing lignocellulosic material, said method comprising contacting lignocellulosic material with at least one xylanase enzyme under conditions where the pH is at least pH 8.5, and wherein said xylanase enzyme is a thermotolerant and alkaliphilic family 10 xylanase.

18. The method of embodiment 17, wherein said xylanase enzyme has an amino acid sequence selected from the group consisting of SEQ ID NOs: 6, 8 or 10 or an active variant or fragment thereof.

19. The method of embodiment 17, wherein the conditions include a reaction temperature of about 95° C.

20. The method of embodiment 17 or 18, wherein the xylanase enzyme is present from about 0.01 units to about 1000 units.

21. The method of embodiment 17 or 18, wherein the xylanase enzyme is present at about 500 units.

22. The method of embodiment 17 or 18, wherein the pH is reduced over time to a pH of about pH 6.

23. The method of embodiment 17 or 18, where the contacting is for about 12 hours to about 24 hours.

24. The method of embodiment 17 or 18, wherein the contacting is for about 6 hours.

25. The method of embodiment 17 or 18, wherein the contacting is in the presence of at least one additional enzyme selected from the group consisting of a cellulase, hemicellulase, ligninase, pectinase and protease.

26. The method of embodiment 25, wherein the cellulase is selected from the group consisting of a mannan endo-1,4-β-mannosidase, 1,3-β-D-glucan glucanohydrolase, 1,3-β-glucan glucohydrolase, 1,3-1,4-β-D-glucan glucanohydrolase and 1,6-β-D-glucan glucanohydrolase.

27. The method of embodiment 25, wherein the hemicellulase is selected from the group consisting of an α-L-arabinofuranosidase, α-glucuronidase, acetyl mannan esterase, acetyl xylan esterase, α-galactosidase, β-glucosidase, β-1,4-xylosidase, endo-galactanase, endo-β-1,4-mannanase, endo-α-1,5-arabinanase, exo-β-1,4-mannosidase, exo-β-1,4-xylosidase, feruloyl esterase, ferulic acid esterase, p-cumaric acid esterase, glucuronoxylan xylanohydrolase and xyloglucan endotransglycosylase.

28. The method of embodiment 25, wherein the ligninase is selected from the group consisting of a diarylpropane peroxidase, glucose oxidase, glyoxal oxidase, lignin peroxidase, manganese peroxidase, methanol oxidase, methanol oxidoreductase, phenol oxidase, phenol peroxidase and veratryl alcohol oxidase.

29. The method of embodiment 25, wherein the pectinase is selected from the group consisting of a pectolyase, pectozyme and polygalacturonase.

30. The method of embodiment 25, wherein the protease is selected from the group consisting of an asclepain, bromelain, caricain, chymopapain, collagenase, glycyl endopeptidase, pepsin, pronase, subtilisin and thermolysin.

31. The method of embodiment 17, 18, or 25, wherein the method further comprises processing with at least one enzyme selected from the group consisting of an amylase, catalase, cutinase, glucanase, glucoamylase, glucose isomerase, lipase, phytase, pullulanase and xylose isomerase.

32. The method of embodiment 17, 18, 25 or 31, wherein the method further comprises processing with at least one agent selected from the group consisting of a chlorine, detergent, hypochlorite, hydrogen peroxide, oxalic acid, peracid, pH-regulating agent, trisodium phosphate, sodium chlorite, sodium nitrate, surfactant, urea and water.

33. The method of embodiment 17, 18, 25, 31 or 32, wherein the method further comprises processing with an ethanologenic microorganism such as a bacteria or yeast.

34. The method of any of embodiments 17 through 33, wherein prior to step (a) the lignocellulosie material is pretreated by biological pretreatment, chemical pretreatment or physical pretreatment.

35. The method of embodiment 34, wherein the biological pretreatment comprises use of lignin-solubilizing microorganisms.

36. The method of embodiment 35, wherein the chemical pretreatment is selected from the group consisting of use of alkaline treatment, ammonia treatment, dilute acid treatment, organic solvent treatment, ozone treatment, sulfur dioxide treatment, carbon dioxide treatment and pH-controlled hydrothermolysis.

37. The method of embodiment 35, wherein the physical pretreatment is selected from the group consisting of use of hydrothermolysis, irradiation, milling, steaming/steam explosion and sonicating (ultra-sonicating).

These and other advantages, features and objects of the present invention will become better understood from the description that follows. The description of exemplary embodiments is not intended to limit the invention to the particular forms disclosed, but on the contrary, the intention is to cover all alternatives, equivalents and modifications falling within the spirit and scope of the invention as defined by the embodiments above and the claims below. Reference should therefore be made to the embodiments above and claims below for interpreting the scope of the invention.

SUMMARY OF THE SEQUENCE LISTING

SEQ ID NO:1 Polynucleotide sequence derived from *Clostridium thermocellum*, gene XynZ holo enzyme SEQ ID NO:2 Polypeptide encoded by SEQ ID NO:1
SEQ ID NO:3 Polynucleotide sequence derived from *Clostridium thermocellum*, gene XynZ ferrulic acid esterase enzyme
SEQ ID NO:4 Polypeptide encoded by SEQ ID NO:3
SEQ ID NO:5 Polynucleotide sequence derived from *Thermotoga maritima*, gene XynA
SEQ ID NO:6 Polypeptide encoded by SEQ ID NO:5
SEQ ID NO:7 Polynucleotide sequence derived from *Thermotoga maritima*, gene XynB
SEQ ID NO:8 Polypeptide encoded by SEQ ID NO:7
SEQ ID NO:9 Polynucleotide sequence derived from *Bacillus*, gene XynA
SEQ ID NO:10 Polypeptide encoded by SEQ ID NO:9

DETAILED DESCRIPTION OF THE INVENTION

Overview

The work described herein is the first to show that xylanases isolated from microorganisms such as thermophilic *Thermotoga* spp. can have activity during chemical pretreatment of lignocellulosic material. That is, the xylanases hydrolyze xylan during the pretreatment process. These enzymes retain significant xylanase activity at a high pH and high temperature. Xylan is a major component of hemicellulose, and together with cellulose and lignin is collectively known as lignocellulose, make up the major constituents of non-woody and woody plants.

As used herein, "lignocellulose" or "lignocellulosic material" means non-woody and woody plant material such as crop, plant and tree biomass comprising polysaccharide polymers such as cellulose, hemicellulose and lignin. Lignocellulosic material also can include crop, plant or tree waste products including agricultural residues such as corn stover and sugarcane bagasse, dedicated energy crop residues, wood residues such as sawmill and paper mill discards, and municipal paper waste.

The compositions and methods described herein therefore can be used to process lignocellulosic material to many useful organic chemicals, fuels and products. For example, some commodity and specialty chemicals that can be produced from lignocellulosic material include, but are not limited to, acetone, acetate, butanediol, cis-muconic acid, ethanol, ethylene glycol, furfural, glycerol, glycine, lysine, organic acids (e.g., lactic acid), 1,3-propanediol, polyhydroxyalkanoates, and xylose. Likewise, animal feed and various food/beverages can be produced from lignocellulosic material. See generally, Lynd et al. (1999) *Biotechnol. Prog.* 15:777-793; Philippidis, "Cellulose bioconversion technology" 179-212 In: *Handbook on Bioethanol: Production and Utilization* (Wyman ed., Taylor & Francis 1996); and Ryu & Mandels (1980) *Enz. Microb. Technol.* 2:91-102. Potential co-production benefits extend beyond the synthesis of multiple organic products from fermentable carbohydrate in lignocellulosic material, as lignin-rich residues remaining after processing can be converted to lignin-derived chemicals or can be used for power production.

Compositions
Enzyme Compositions

Compositions of the invention include at least one xylanase enzyme or active variant or fragment thereof where the compositions are active at a high pH. By "high pH" is intended a pH of at least about pH 8.5, including about pH 9.0, about pH 9.5, about pH 10.0, about pH 10.5, about pH 11.0, about pH 11.5, about pH 12.0, about pH 12.5 or higher. Other components can be included within the compositions including other enzymes.

The xylanase enzymes of the invention are family 10 xylanases that are thermotolerant and alkaliphilic. By "thermotolerant" is meant that the enzyme retains at least 70% of its activity after 30 minutes at 60° C. By "alkaliphilic" is intended that the enzyme retains at least 80% of its activity after 30 minutes at a pH of 8.5.

Xylanases are a large family of hydrolytic enzymes. As used herein, "xylanase" or "xylanases" means an enzyme capable of at least hydrolyzing xylan to xylobiose and xylobiose. Because of the heterogeneity and complexity of xylan, xylanases are quite diverse in their folding patterns (i.e., primary sequence variations), hydrolytic activities (i.e., yields, rates and products), mechanisms of action, substrate specificities and physicochemical characteristics. See, *Methods in Plant Biochemistry and Molecular Biology* (Dashek ed., CRC Press 1997); and Collins et al. (2005) *FEMS Microbiol. Rev.* 29:3-23. The official name for xylanase is endo-1, 4-β-xylanase; however, it also is known in the art as endoxylanase, 1,4-β-D-xylan-xylanohydrolase, endo-1,4-β-D-xylanase, β-1,4-xylanase and β-xylanase.

Xylanases are classified with other glycosidases by primary structure comparisons of the catalytic domains and grouped in families of related sequences. See, Henrissat et al. (1989) *Gene* 81:83-95; and Henrissat et al. (2001) *Methods Enzymol.* 330:183-201. Within this classification system, xylanases are typically confined to families 10 and 11. Because of commercial demands for xylanases in feed, food/beverage and technical industries, a number of extremophilic xylanases have been isolated, especially xylanases from acidophilic, alkaliphilic and thermophilic bacteria.

Of interest herein are high-temperature (i.e., thermostable) and high-pH (i.e., alkaliphilic) tolerant xylanases isolated from microorganisms such as bacteria that exhibit xylanase activity. Such xylanase enzymes are family 10 xylanases. In one embodiment, the xylanase can be from a *Thermotoga* sp. *Environ. Microbial.* 61:4403-4408. Nucleotide and amino acid sequences for this enzyme are set forth in SEQ ID NOs:5 and 7, respectively.

Examples of other bacteria from which such xylanases can be isolated include, but are not limited to, *Bacillus* spp. such as *Bacillus firmus* (GenBank® Accession No. AAQ83581), *Bacillus halodurans* S7 (GenBank® Accession No. AAV98623), *Bacillus halodurans* C-125 (GenBank® Accession No. BAA00055), *Bacillus* sp. strain NG-27 (GenBank® Accession No. AAB70918) and *Bacillus stearothermophilus* T-6 (GenBank® Accession No. ABI49951); and *Thermotoga* spp. such as *Thermotoga maritima* (GenBank® Accession No. AAD35164). See also, Chang et al. (2004) *Biochem.*

*Biophys. Res. Commun.* 319:1017-1025; Gat et al. (1994) *Appl. Environ. Microbial.* 60:1889-1896; Gupta et al. (2000) *Appl. Environ. Microbial.* 66:2631-2635; Hamamoto et al. (1987) *Agr. Biol. Chem.* 51:953-955; Horikoshi (1999) *Microbial. Mol. Biol. Rev.* 63:735-750; Jiang et al. (2006) *Appl. Microbial. Biotechnol.* 70:65-71; and Mamo et al. (2006) *Mol. Biotechnol.* 33:149-159.

These enzymes show optimal xylanase activity at high temperatures and are thermostable. Half-life of the enzymes at 85° C. can be about 24 hours and 6.5 hours at pH 6.8 and pH 9.3, respectively. The enzymes also show substantial xylanase activity across a broad pH range and are alkaliphilic.

The xylanase enzymes are thermotolerant and thermoactive. "Thermotolerant" as used herein describes an enzyme which has a melting temperature that is greater than 60 degrees C. "Thermoactive" as used here describes an enzyme which has optimal activity at greater than 60 degrees C. A thermotolerant xylanase enzyme retains at least about 70% activity at about 60° C. for 30 minutes, at least about 65% activity at about 70° C. for 30 minutes, at least about 60% activity at about 80° C. for 30 minutes. The enzymes retain xylanase activity at temperatures up to about 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., or more.

As used herein, "alkaliphilic" means that the enzyme retains at least about 70% activity at pH 8.5, retains at least 65% activity at pH 9.0, retains 60% activity at pH 10.0. The xylanase enzyme retains activity at pH 12.0 or higher.

As used herein, "about" means within a statistically meaningful range of a value such as a stated concentration, time frame, molecular weight, volume, temperature or pH. Such a range can be within an order of magnitude, typically within 20%, more typically still within 10%, and even more typically within 5% of a given value or range. The allowable variation encompassed by "about" will depend upon the particular system under study, and can be readily appreciated by one of skill in the art.

While a full-length enzyme can be used in the compositions, active variants and fragments thereof also can be used. As used herein, "variant" means an enzyme having a substantially similar amino acid sequence to a reference enzyme sequence such as, for example, SEQ ID NOs: 6, 8 or 10. A variant also includes a nucleic acid molecule having a substantially similar nucleotide sequence to one encoding the reference enzyme such as, for example, SEQ ID NOs: 5, 7 or 9. For molecules such as enzymes, a variant can include an addition or deletion of one or more amino acids at one or more internal sites in the amino acid sequence of the reference enzyme and/or substitution of one or more amino acid residues at one or more sites in the amino acid sequence of the reference enzyme. The variant can be active and therefore continue to possess the desired activity of the reference enzyme such as xylanase activity as described herein. The variant can result from, for example, a genetic polymorphism or human manipulation. An active variant of the reference enzyme can have at least about 40%, 45%, 50%, 55%, 60%, 65%, 70%, 75%, 80%, 85%, 90%, 91%, 92%, 93%, 94%, 95%, 96%, 97%, 98%, 99%, or more sequence identity to the amino acid sequence for the reference enzyme as determined by sequence alignment programs and parameters described elsewhere herein. An active variant can differ from the reference enzyme sequence by as few as 1-15 amino acid residues, as few as 1-10, such as 6-10, as few as 5, as few as 4, 3, 2, or even 1 amino acid residue.

A variant can be altered from the reference enzyme in various ways including nucleotide or amino acid deletions, insertions, substitutions and truncations. Methods for such manipulations are well known in the art.

For example, amino acid sequence variants of the reference enzyme can be prepared by mutating the nucleotide sequence encoding the enzyme. Methods for mutagenesis and nucleotide sequence alterations are well known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Guidance as to appropriate amino acid substitutions that do not affect biological activity of the reference enzyme may be found in the model of Dayhoff et al., *Atlas of Protein Sequence and Structure* (National Biomedical Research Foundation 1978).

The deletions, insertions and substitutions of the enzymes are not expected to produce radical changes in its characteristics. However, when it is difficult to predict the exact effect of the substitution, deletion or insertion in advance of doing so, one of skill in the art will appreciate that the effect can be evaluated by assays for xylanase activity.

Assays for xylanase activity are well known in the art. See, e.g., Bailey et al. (1992) *J. Biotechnol.* 23:257-270; Ge et al. (2007) *Anal. Biochem.* 362:63-68; Gibbs et al. (1995), supra; Jeffries et al. (1998) *Appl. Biochem. Biotechnol.* 70-72:257-265; Kenealy & Jeffries (2003) *Biotechnol. Lett.* 25:1619-1623; Miller (1959) *Anal. Chem.* 31:426-428; Taguchi et al. (1996) *Biosci. Biotechnol. Biochem.* 60:983-985; Teather & Wood (1982) *Appl. Environ. Microbiol.* 43:777-780; and Wang & Broda (1992) *Appl. Environ. Microbiol.* 58:3433-3436. Likewise, kits for assaying xylanase activity are commercially available, for example, from Invitrogen (Carlsbad, Calif.) and Megazyme Int'l Ireland Ltd. (Wicklow, Ireland).

As noted above, the compositions can use active fragments of the xylanase enzyme. As used herein, "fragment" means a portion of the reference enzyme that retains xylanase activity. A fragment also means a portion of a nucleic acid molecule encoding the reference enzyme. An active fragment of the enzyme can be prepared, for example, by isolating a portion of an enzyme-encoding nucleic acid molecule, expressing the encoded fragment of the enzyme (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1,000, 1,100, 1,200, 1,300 or 1,400 contiguous nucleotides, or up to the number of nucleotides present in a full-length enzyme-encoding nucleic acid molecule. As such, polypeptide fragments can be at least about 50, 60, 70, 80, 90, 100, 125, 150, 175, 200, 225 or 250 contiguous amino acid residues, or up to the total number of amino acid residues present in the full-length enzyme.

Determining percent sequence identity between any two sequences can be accomplished using a mathematical algorithm. Non-limiting examples of such mathematical algorithms are the algorithm of Myers & Miller (1988) CABIOS 4:11-17; the local alignment algorithm of Smith et al. (1981) *Adv. Appl. Math.* 2:482-489; the global alignment algorithm of Needleman & Wunsch (1970) *J. Mol. Biol.* 48:443-453; the search-for-local alignment method of Pearson & Lipman (1988) *Proc. Natl. Acad. Sci. USA* 85:2444-2448; the algorithm of Karlin & Altschul (1990) *Proc. Natl. Acad. Sci. USA* 87:2264-2268, modified as in Karlin & Altschul (1993) *Proc. Natl. Acad. Sci. USA* 90:5873-5877.

Computer implementations of these mathematical algorithms can be used to compare sequences to determine sequence identity. Such implementations include, but are not limited to, CLUSTAL in the PC/Gene Program (Intelligenetics; Mountain View, Calif.); the ALIGN Program (Version 2.0; Corpet et al. (1988) *Nucleic Acids Res.* 16:10881-10890; Higgins et al. (1988) *Gene* 73:237-244; Higgins et al. (1989) *CABIOS* 5:151-153; Huang et al. (1992) *CABIOS* 8:155-165; and Pearson et al. (1994) *Meth. Mol. Biol.* 24:307-331) and GAP, BESTFIT, BLAST, PASTA and TFASTA in the GCG Wisconsin Genetics Software Package, Version 10 (Accelrys Inc.; San Diego, Calif.). Alignments using these programs can be performed using the default parameters.

As used herein, "sequence identity" or "identity" in the context of two nucleotide or amino acid sequences means that the residues in the two sequences that are the same when aligned for maximum correspondence over a specified region. When percentage of sequence identity is used in reference to proteins such as enzymes it is recognized that residue positions that are not identical often differ by conservative amino acid substitutions, where amino acid residues are substituted for other amino acid residues with similar chemical properties (e.g., charge or hydrophobicity) and therefore do not change the functional properties of the enzyme. When sequences differ in conservative substitutions, the percent sequence identity can be adjusted upwards to correct for the conservative nature of the substitution. Sequences that differ by such conservative substitutions are said to have "sequence similarity" or "similarity." Means for making this adjustment are well known to one of skill in the art. The scoring of conservative substitutions is calculated, for example, as implemented in the PC/GENE Program.

As used herein, "percentage of sequence identity" means a value determined by comparing two optimally aligned sequences over a defined region, wherein the portion of the nucleotide or amino acid sequence in the defined region may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the window of comparison, and multiplying the result by 100 to yield the percentage of sequence identity.

As such, the xylanase enzymes can be provided in the composition as a partially or fully purified full-length enzyme, or as an active variant or fragment thereof, or even can be provided as an enzyme-producing microorganism, plant, plant part or plant host cell. Complete purification is not required in any case. The enzyme, variant or fragment therefore can be at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% pure, or more.

Methods of purifying polypeptides and proteins such as enzymes are well known in the art. See, e.g., Cesar & Mrša (1996) *Enzyme Microb. Tech.* 19:289-296; Chivero et al. (2001) *Food Chem.* 72:179-185; de Albuquerque Lucena-Neto et al. (2004) *Br. J. Microb.* 35:86-90; Ehle & Horn (1990) *Bioseparation* 1:97-110; Gupta et al. (2002) *Biotechnol. Lett.* 24:2005-2009; Hengen (1995) *Trends Biochem Sci.* 20:285-286; Kanda et al. (1985) *J. Biochem.* 98:1545-1554; Khasin et al. (1993) *Appl. Environ. Microb.* 59:1725-1730; Kudo et al. (1985) *J. Gen. Microbial.* 131:2825-2830; Regnier (1983) *Science* 222:245-252; Roy & Uddin (2004) *Pak J. Biol. Sci.* 7:372-379; Royer & Nakas (1991) *Eu. J. Biochem.* 202:521-529; Sá-Pereira et al. (2003) *Mol. Biotechnol.* 24:257-281; Shaw, "Peptide purification by reverse-phase HPLC" 257-287 In: *Methods in Molecular Biology*, Vol. 32 (Walker ed., Humana Press 1994); Simpson et al. (1991) *Biochem. J.* 277:419-417; *Encyclopedia of Chemical Technology*, $52^{nd}$ ed. (Kirk-Othmer ed., Wiley-Interscience 2007); *Basic Methods in Protein Purification and Analysis: A Laboratory Manual* (Simpson et al. eds., Cold Spring Harbor Laboratory Press 2008); *Enzyme Purification and Related Techniques. Methods in Enzymology*, Vol. 22 (Jakoby ed., Academic Press Inc. 1971) *Methods in Enzymology: Affinity Techniques—Enzyme Purification: Part B: Vol. 34: Affinity Techniques Part B* (Kaplan et al. eds., Elsevier 1974); as well as US Patent Application Publication Nos. 2009/0137022 and 2009/0239262; and U.S. Pat. Nos. 4,347,322; 4,634,673; 4,725,544 and 5,437,992. Examples of purification techniques suitable for enzymes include, but are not limited to, precipitation such as ammonium sulfate precipitation, separation based on molecular size such as gel filtration, separation based on charge such as ion-exchange chromatography, separation based on specific interaction with other biomolecules such as bio-affinity chromatography or antibody recognition of amino acid sequence, and separation based on other principles such as hydrophobic interaction chromatography or hydroxyapatite chromatography.

Whether the compositions include a full-length xylanase enzyme, or an active variant or fragment thereof, they can include about 0.01 units to about 1000 units, about 0.1 units to about 500 units or about 1 unit to about 50 units of enzyme activity per gram of lignocellulosic material to be treated. Alternatively, the compositions can include about 1 unit to about 10 units, about 10 units to about 100 units, about 100 units to about 200 units, about 200 units to about 300 units, about 300 units to about 400 units, about 400 units to about 500 units, about 500 units to about 600 units, about 600 units to about 700 units, about 700 units to about 800 units, about 800 units to about 900 units, about 900 units to about 1000 units, or more of enzyme activity per gram of lignocellulosic material to be treated. One unit can be defined as an amount of enzyme required to liberate 1 μmmol of xylose per minute at an assay temperature. If using a reducing sugar assay for determining xylanase activity, one unit can be defined as an amount of enzyme required to liberate 1 micro-mole of xylose equivalent per minute at an assay temperature.

The compositions may comprise the xylanase enzyme, variant or fragment thereof only, or can be a mixture (i.e., "cocktail") having the xylanase enzyme, variant or fragment thereof and at least one or more other enzyme(s) including other lignocellulolytic enzymes useful in processing lignocellulosic materials such as other cellulases, hemicellulases, ligninases, pectinases and proteases. As used herein, "lignocellulolytic enzyme" means an enzyme that processes lignocellulosic material such as cellulose, hemicellulose and lignin, as well as other polysaccharide and protein components that may be a part of or associated with lignocellulose.

Examples of cellulases include, but are not limited to, mannan endo-1,4-β-mannosidase, 1,3-β-D-glucan glucanohydrolase, 1,3-β-glucan glucohydrolase, 1,3-1,4-β-D-glucan glucanohydrolase and 1,6-β-D-glucan glucanohydrolase.

Examples of hemicellulases include, but are not limited to, α-L-arabinofuranosidase, α-glucuronidase, acetyl mannan esterase, acetyl xylan esterase, α-galactosidase, β-glucosidase, β-1,4-xylosidase, endo-galactanase, endo-β-1,4-mannanase, endo-α-1,5-arabinanase, exo-β-1,4-mannosidase, exo-β-1,4-xylosidase, feruloyl esterase, ferulic acid esterase, p-cumaric acid esterase, glucuronoxylan xylanohydrolase and xyloglucan endotransglycosylase.

Examples of ligninases include, but are not limited to, diarylpropane peroxidase, glucose oxidase, glyoxal oxidase, lignin peroxidase (LiP), manganese peroxidase, methanol oxidase, methanol oxidoreductase, phenol oxidase (laccase), phenol peroxidase and veratryl alcohol oxidase.

Examples of pectinases include, but are not limited to, pectolyase, pectozyme and polygalacturonase.

Examples of proteases include, but are not limited to, asclepain, bromelain, caricain, chymopapain, collagenase, glycyl endopeptidase, pepsin, pronase, subtilisin and thermolysin.

The compositions also can include other enzymes such as amylase, catalase, cutinase, glucanase, glucoamylase, glucose isomerase, lipase, phytase, pullulanase and xylose isomerase.

As above, any of these enzymes can be provided as partially or fully purified full-length enzymes, or active variants or fragments thereof, or can be provided as an enzyme-producing microorganism. Moreover, any of these enzymes can be provided in an amount effective to hydrolyze their substrate, such as in amounts from about 0.001 wt. % to about 50 wt. %, from about 0.01 wt. % to about 50 wt. %, from about 0.1 wt. % to about 50 wt. %, from about 1 wt. % to about 50 wt. %, from about 10 wt. % to about 50 wt. %, from about 20 wt. % to about 50 wt. %, from about 30 wt. % to about 50 wt. %, from about 40 wt. % to about 50 wt. %, or more.

The compositions also can include agents typically used in processing lignocellulosic materials such as a chlorine, detergent, hypochlorite, hydrogen peroxide, oxalic acid, peracid, pH-regulating agent, trisodium phosphate, sodium chlorite, sodium nitrate, surfactant, urea and water.

Examples of detergents include, but are not limited to, anionic, cationic or neutral detergents such as Nonidet (N)P-40, sodium dodecyl sulfate (SDS), sodium lauryl sulfate (SLS), sulfobetaine, n-octylglucoside, deoxycholate, Triton® X-100 (Dow Chemical Co.; Midland, Mich.) and Tween® 20 (ICI Americas, Inc.; Bridgewater, N.J.).

Examples of peracids include, but are not limited to, meta-chloroperoxybenzoic acid, perbenzoic acid, perchloric acid, perphthalic acid, permaleic acid, peracetic acid, performic acid, perproprionic acid and p-nitro perbenzoic acid.

Examples of surfactants include, but are not limited to, a secondary alcohol ethoxylate, fatty alcohol ethoxylate, nonylphenol ethoxylate, phosphate ester of fatty alcohols, polyoxyethylene ether, polyethylene glycol, polyoxyethylenated alkyl phenol and stearic acid and tridecyl ethoxylate.

Any of these agents can be provided as partially or fully purified. Moreover, any of these agents can be provided in an amount from about 0.001 wt. % to about 50 wt. %, from about 0.01 wt. % to about 50 wt. %, from about 0.1 wt. % to about 50 wt. %, from about 1 wt. % to about 50 wt. %, from about 10 wt. % to about 50 wt. %, from about 20 wt. % to about 50 wt. %, from about 30 wt. % to about 50 wt. %, from about 40 wt. % to about 50 wt. %, or more.

The compositions also can include microorganisms, especially ethanologenic and/or lignin-solubilizing microorganisms such as bacteria or yeast. See generally, Burchhardt & Ingram (1992) *Appl. Environ. Microbiol.* 58:1128-1133; Dien et al. (1998) *Enzyme Microb. Tech.* 23:366-371; Keating et al. (2004) *Enzyme Microb. Tech.* 35:242-253; Lawford & Rousseau (1997) *Appl. Biochem. Biotechnol.* 63-65:221-241; *Handbook on Bioethanol: Production and Utilization* (Wyman ed., CRC Press 1996); as well as US Patent Application Publication Nos. 2009/0246841 and 2009/0286293; and U.S. Pat. No. 6,333,181. Such microorganisms can express enzymes that assist in processing lignocellulosic material such as alcohol dehydrogenase, pyruvate decarboxylase, transaldolase, transketolasepyruvate decarboxylase, xylose reductase, xylitol dehydrogenase or xylose isomerase xylulokinase. Examples of such microorganisms include, but are not limited to, members in genera such as *Candida, Erwinia, Escherichia, Klebsiella, Pichia, Saccharomyces, Streptomyces* and *Zymomonas*. See, e.g., Dien (1998), supra; Ingram & Conway (1988) *Appl. Environ. Microbiol.* 54:397-404; Jarboe et al. (2007) *Adv. Biochem. Engin./Biotechnol.* 108:237-261; Keating et al. (2004) *J. Indust. Microbiol. Biotech.* 31:235-244; Keating et al. (2006) *Biotechnol. Bioeng.* 93:1196-1206; Pasti et al. (1990) *Appl. Environ. Microbiol.* 56:2213-2218; and Zhang et al. (1995) *Science* 267:240-243.

The compositions having the enzyme, variant or fragment thereof, as well as any of the other enzymes and/or agents described above, can be prepared as a liquid, slurry, solid or gel.

Transgenic Organisms

Compositions of the invention include plants, plant parts and plant host cells transformed with a nucleic acid construct encoding at least one xylanase enzyme, or a variant or fragment thereof having xylanase activity. As used herein, "plant part" means non-woody and woody plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes, and the like. The transformed plants are intended for use in the production of celluolosic ethanol. The transgenic plants of the invention will serve as the source of xylanase enzyme activity in the lignocellulose conversion process. The transgenic plants of the invention can be used in combination with other transgenic plants containing other enzymes, for example AMY797E, a transgenic plant expressing a thermostable α-amylase.

Examples of plants include, but are not limited to, barley, beans in general, *Brassica* spp., clover, cocoa, coffee, cotton, flax, maize, millet, peanut, rape/canola, rice, rye, safflower, sorghum, soybean, sugarcane, sugar beet, sunflower, sweet potato, tea and wheat; vegetables such as broccoli, brussel sprouts, cabbage, carrot, cassaya, cauliflower, cucurbits, lentils, lettuce, pea, peppers, potato, radish and tomato; grasses such as alfafa, bermudagrass, elephantgrass, rhodesgrass, tall fescue grass, tall wheat grass, *Miscanthus* spp. and switchgrass; tree fruits such as apples, apricots, avocado, banana, citrus, coconuts, pears, peaches, pineapple and walnuts; and flowers such as carnations, orchids and roses.

To prevent the negative phenotype associated with the expression of a xylanase enzyme in plants, it is recognized that care will need to be taken to control the expression, activation, or localization of the xylanase enzyme in plants. As discussed further herein, one method of controlling the negative phenotype is to sequester the expressed xylanase enzyme in the plant. In particular, signal sequences or targeting sequences can be used to target the enzyme to organelles such as the vacuole, the endoplasmic reticulum, the chloroplast, and the like. In this manner, a signal or targeting sequence is operably linked to the xylanase enzyme. Therefore, a DNA construct or expression cassette for expression of the enzyme in a plant will include a signal sequence operably linked to the coding sequence for the xylanase enzyme. Such targeting sequences will target the xylanase enzyme to a vacuole, the endoplasmic reticulum, the chloroplast, and the like.

Examples of such sequences include, but are not limited to, the transit peptide for the acyl carrier protein, the small subunit of RUBISCO, plant EPSP synthase, and the like. See, e.g. Archer et al. (1990) *J. Bioenerg. Biomemb.* 22:789-810);

Clark et al. (1989) *J. Biol. Chem.* 264:17544-17550; Daniell (1999) *Nat. Biotech.* 17:855-856; de Castro Silva Filho et al. (1996) *Plant Mol. Biol.* 30:769-780; Della-Cioppa et al. (1987) *Plant Physiol.* 84:965-968; Lamppa et al. (1988) *J. Biol. Chem.* 263:14996-14999; Lawrence et al. (1997) *J. Biol. Chem.* 272:20357-20363; Romer et al. (1993) *Biochem. Biophys. Res. Commun.* 196:1414-1421; Schmidt et al. (1993) *J. Biol. Chem.* 268:27447-27457; Schnell et al. (1991) *J. Biol. Chem.* 266:3335-3342); Shah et al. (1986) *Science* 233:478-481; Von Heijne et al. (1991) *Plant Mol. Biol. Rep.* 9:104-126; and Zhao et al. (1995) *J. Biol. Chem.* 270:6081-6087; as well as U.S. Pat. No. 6,338,168.

Endoplasmic reticulum signal peptides include those described in Raikhel & Chrispeels "Protein sorting and vesicle traffic" In: *Biochemistry and Molecular Biology of Plants* (Buchanan et al. eds., American Society of Plant Physiologists 2000). See also, Denecke et al. (1992) *EMBO J.* 11:2345-2355; Denecke et al. (1993) *J. Exp. Bot.* 44:213-221; Gomord et al. (1996) *Plant Physiol. Biochem.* 34:165-181; Lehmann et al. (2001) *Plant Physiol.* 127:436-449; Munro & Pelham (1986) *Cell* 46:291-300; Munro & Pelham (1987) *Cell* 48:899-907; Vitale et al. (1993) *J. Exp. Bot.* 44:1417-1444; and Wandelt et al. (1992) *Plant J.* 2:181-192.

In some instances, it may be desirable to localize the xylanase enzyme within a vacuole. For vacuole-targeted expression of xylanase enzymes, plants are transformed with vectors that include a vacuolar targeting sequence such as that from a tobacco chitinase gene. Vacuole sorting signal sequences include the barley polyamino oxidase 2 (BPAO2) signal sequence (Cervelli et al. (2004) *The Plant Journal* 40:410-418). For other vacuole sorting signals, see U.S. application Ser. No. 12/359,421 and Raikhel & Chrispeels (2000), supra.

Plastid-targeting sequences are well known in the art and can be used in the practice of the invention. See, e.g., Clark et al. (1989). *J. Biol. Chem.* 264:17544-17550; Della-Cioppa et al. (1987), supra; Romer et al. (1993) *Biochem. Biophys. Res. Commun.* 196:1414-1421; Shah et al. (1986) *Science* 233: 478-481; and Von Heijne et al. (1991) *Plant Mol. Biol. Rep.* 9:104-126. Additional chloroplast-targeting sequences include the chloroplast small subunit of ribulose-1,5-bisphosphate carboxylase (Rubisco) (de Castro Silva Filho et al. (1996) *Plant Mol. Bial.* 30:769-780; and Schnell et al. (1991) *J. Biol. Chem.* 266:3335-3342); 5-(enolpyruvyl)shikimate-3-phosphate synthase (EPSPS) (Archer et al. (1990), supra); tryptophan synthase (Zhao et al. (1995), supra); plastocyanin (Lawrence et al. (1997), supra); chorismate synthase (Schmidt et al. (1993), supra); and the light harvesting chlorophyll a/b binding protein (LHBP) (Lamppa et al. (1988), supra). One of skill in the art also can envision generating transgenic plants in which the chloroplasts have been transformed to overexpress the xylanase enzyme. See, e.g., Daniell (1999) *Nat. Biotech.* 17:855-856; as well as U.S. Pat. No. 6,338,168.

Methods for transforming chloroplasts are well known in the art. See, e.g., Svab et al. (1990) *Proc. Natl. Acad. Sci. USA* 87:8526-8530; Svab & Maliga (1993) *Proc. Natl. Acad. Sci. USA* 90:913-917; Svab & Maliga (1993) *EMBO J.* 12:601-606. Likewise, nucleotide sequences to be targeted to the chloroplast can be optimized for expression in the chloroplast to account for differences in codon usage between the plant nucleus and this organelle. In this manner, the polynucleotide of interest may be synthesized using chloroplast-preferred codons. See, e.g., U.S. Pat. No. 5,380,831.

For localization of the xylanase enzyme within the apoplast, an apoplast-targeting sequence such as a maize γ-zein N-terminal signal sequence (U.S. Pat. No. 7,102,057) can be used.

Additional guidance on targeting polypeptides can be found, for example, in Bruce (2001) *Biochim Biophys Acta* 1541:2-21; Emanuelsson et al. (2000) *J. Mol. Biol.* 300:1005-1016; Emanuelsson & von Heijne (2001) *Biochim Biophys Acta* 1541:114-119; Hadlington & Denecke (2000) *Curr. Opin. Plant Biol.* 3:461-468; Nicchitta (2002) *Curr. Opin. Cell Biol.* 14:412-416; and Silva-Filho (2003) *Curr. Opin. Plant Biol.* 6:589-595.

Briefly, methods of expressing a nucleotide sequence in a plant part such as a plant host cell include transforming the plant host cell with, for example, a nucleic acid construct such as an expression cassette having a coding sequence for a xylanase enzyme, variant or fragment thereof operably linked to one or more regulatory sequences. Coding sequence for some embodiments of the xylanase enzyme include the nucleotide sequences set forth in SEQ ID NOs: 5, 7 or 9 or a fragment or variant thereof, or the polypeptide sequences set forth in SEQ ID NOs: 6, 8 or 10 or a fragment or variant thereof. The transformed plant host cell is grown under conditions where the nucleotide sequence is expressed in the plant host cell. In some instances, the methods include an additional step of regenerating the transformed plant host cell into a morphologically normal, fertile plant.

As used herein, "expression cassette" means a nucleic acid molecule having at least a control sequence operably linked to a coding sequence of interest (e.g., the xylanase enzyme). In this manner, plant promoters in operable interaction with the nucleotide sequences for the xylanase enzyme are provided in expression cassettes for expression in a plant, plant part or plant host cell.

A plant, plant part or plant host cell expressing the xylanase enzyme therefore can be obtained by introducing into the plant, plant part or plant host cell a coding sequence for the xylanase enzyme. Preferably, the coding sequence can be present in an expression cassette or another nucleic acid construct such as a vector.

Expression of the coding sequence of interest in the expression cassette can be under the control of a constitutive promoter or an inducible promoter that initiates transcription only when the host cell is exposed to some particular external stimulus. Alternatively, the expression cassette can be under the control of a tissue-specific promoter that functions in a particular tissue, organ or even stage of development.

For purposes of the invention, the regulatory regions (i.e., promoters, transcriptional regulatory regions, and translational termination regions) may be native/analogous to the host cell or to each other. Alternatively, the regulatory regions may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The choice of promoters to be used depends upon several factors, including, but not limited to, cell- or tissue-specific expression, desired expression level, efficiency, inducibility and selectability. For example, where expression in specific tissues or organs is desired, tissue-specific promoters can be used. In contrast, where expression in response to a stimulus is desired, inducible promoters can be used. Where continuous expression is desired throughout the cells of a plant, constitutive promoters can be used. It is a routine matter for one of skill in the art to modulate the expression of a nucleotide sequence by appropriately selecting and positioning promoters and other regulatory regions relative to that sequence.

Therefore, in some instances, constitutive promoters can be used. Examples of constitutive promoters include, but are not limited to, the rice actin I promoter (Wang et al. (1992) *Mol. Cell. Biol.* 12:3399-3406; as well as U.S. Pat. No. 5,641, 876), CaMV 35S promoter (Odell et al (1985) Nature 313: 810-812), CaMV 19S promoter (Lawton et al. (1987) *Plant Mol. Biol.* 9:315-324), nos promoter (Ebert et al. (1987) *Proc. Natl. Acad Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter.

Moreover, several tissue-specific regulated genes and/or promoters have been reported in plants. Some reported tissue-specific genes include those encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other genes expressed during embryo development (such as Bce4, see, e.g., Kridl et al. (1991) *Seed Sci. Res.* 1:209-219; as well as EP Patent No. 255378). Additional examples of tissue-specific promoters include, but are not limited to, the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" 29-39 In: *Genetic Engineering of Plants* (Hollaender ed., Plenum Press 1983); and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) Nature 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612). Particularly useful for seed-specific expression is the pea vicilin promoter (Czako et al. (1992) *Mol. Gen. Genet.* 235:33-40; as well as U.S. Pat. No. 5,625,136). Other useful promoters for expression in mature leaves are those that are switched on at the onset of senescence, such as the SAG promoter from *Arabidopsis* (Gan et al. (1995) *Science* 270:1986-1988).

In some instances, inducible promoters can be used. Examples of inducible promoters include, but are not limited to, tetracycline repressor system promoters, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters. Other inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108.

In addition to the promoters described above, the expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences and polyadenylation signal sequences.

The expression cassette also can include a transcriptional and/or translational termination region (i.e., termination region) that is functional in plants. A variety of transcriptional terminators are available for use in expression cassettes and are responsible for the termination of transcription beyond the transgene and correct mRNA polyadenylation. The termination region may be native with the transcriptional initiation region, may be native with the operably linked nucleotide sequence of interest, may be native with the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and the pea rbcs E9 terminator. These can be used in both monocotyledons and dicotyledons. In addition, a coding sequence's native transcription terminator can be used.

As discussed above, to prevent the negative phenotype associated with expression of a xylanase enzyme in a plant, signal sequence may be operably linked to the enzyme to direct the enzyme into a cellular compartment. In this manner, the expression cassette will comprise a coding sequence for the xylanase enzyme operably linked to a nucleic acid sequence for the signal sequence. The signal sequence may be operably linked at the N- or C-terminus of the enzyme.

Regardless of the type of regulatory sequence(s), they can be operably linked to the coding sequence for the xylanase enzyme. As used herein, "operably linked" means that elements of a nucleic acid construct such as an expression cassette are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. Thus, for example, intervening untranslated, yet transcribed, sequences can be present between a promoter and a coding sequence, and the promoter sequence can still be considered "operably linked" to the coding sequence.

The expression cassette also can include a nucleotide sequence for a selectable marker, which can be used to select transformed plant host cells. As used herein, "selectable marker" means a molecule that imparts a distinct phenotype to host cells expressing the marker and thus allows such transformed host cells to be distinguished from cells that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a neo or nptII gene that confers resistance to kanamycin, G418, and the like (Potrykus et al. (1985) *Mol. Gen. Genet.* 199:183-188); a bar gene that confers resistance to phosphinothricin; an altered 5-enolpyruvylshikimate-3-phosphate (EPSP) synthase gene that confers resistance to glyphosate (Hinchee et al. (1988) *Biotech.* 6:915-922); a nitrilase gene such as bxn from *Klebsiella ozaenae* that confers resistance to bromoxynil (Stalker et al. (1988) *Science* 242:419-423); an altered acetolactate synthase (ALS) gene that confers resistance to imidazolinone, sulfonylurea or other ALS-inhibiting chemicals (EP Patent Application No. 154204); a methotrexate-resistant dihydrofolate reductase (DHFR) gene (Thillet et al. (1988) *J. Biol. Chem.* 263:12500-12508); a dalapon dehalogenase gene that confers resistance to dalapon; a mannose-6-phosphate isomerase gene (also referred to as phosphomannose isomerase (PMI)) that confers an ability to metabolize mannose (U.S. Pat. Nos. 5,767,378 and 5,994,629); an altered anthranilate synthase gene that confers resistance to 5-methyl tryptophan; or an hph gene that confers resistance to hygromycin. One of skill in the art is capable of selecting a suitable selectable marker for use in the expression cassette.

Additional selectable markers include, but are not limited to, a β-glucuronidase or uidA gene (GUS) that encodes an enzyme for which various chromogenic substrates are known; an R-locus gene that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a β-lactamase gene that encodes an enzyme for which various chromogenic substrates are known (e.g., PADAC, a chromogenic cephalosporin) (Sutcliffe (1978) *Proc. Natl. Acad. Sci. USA* 75:3737-3741); a xylE gene that encodes a catechol dioxygenase (Zukowsky et al. (1983) *Proc. Natl. Acad. Sci. USA* 80:1101-1105); a tyrosinase gene that encodes an enzyme capable of oxidizing tyrosine to DOPA and dopaquinone, which in turn condenses to form melanin (Katz et al. (1983) *J. Gen. Microbiol.* 129: 2703-2714); a β-galactosidase gene that encodes an enzyme for which there are chromogenic substrates; a luciferase (lux) gene that allows for bioluminescence detection (Ow et al. (1986) *Science* 234:856-859); an aequorin gene that may be employed in calcium-sensitive bioluminescence detection (Prasher et al. (1985) *Biochem. Biophys. Res. Comm.* 126: 1259-1268); or a green fluorescent protein gene (Niedz et al. (1995) *Plant Cell Reports* 14:403-406).

The expression cassette also can include coding sequences for other lignocellulolytie enzymes. Such sequences can be stacked with any combination of nucleotide sequences to create plants, plant parts or plant host cells having the desired phenotype. Stacked combinations can be created by any method including, but not limited to, cross breeding plants by any conventional methodology, or by genetic transformation. If stacked by genetically transforming the plants, the nucleotide sequences of interest can be combined at any time and in any order. For example, a transgenic plant comprising one or more desired traits can be used as the target to introduce further traits by subsequent transformation. The nucleotide sequences can be introduced simultaneously in a co-transformation protocol with coding sequences for the xylanase enzyme provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Intl Patent Application Publication Nos. WO 99/25821; WO 99/25854; WO 99/25840; WO 99/25855 and WO 99/25853.

The expression cassette also can include a coding sequence for one or more polypeptides for agronomic traits that primarily are of benefit to a seed company, grower or grain processor, for example, bacterial pathogen resistance, fungal resistance, herbicide resistance, insect resistance, nematode resistance and virus resistance. See, e.g., U.S. Pat. Nos. 5,304, 730; 5,495,071; 5,569,823; 6,329,504 and 6,337,431. The trait also can be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). Various traits of interest, as well as methods for introducing these traits into a plant, are described, for example, in U.S. Pat. Nos. 4,761,373; 4,769,061; 4,810,648; 4,940,835; 4,975, 374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Application Publication No. 2001/0016956. See also, on the World Wide Web at lifesci.sussex.ac.uk/home/Neil_Crickmore/Bt/.

Numerous nucleotide sequences are known to enhance gene expression from within a transcriptional unit, and these sequences can be used in conjunction with the coding sequence for the xylanase enzyme to increase its expression in transgenic plants. For example, introns of the maize Adhl gene and Intron 1 have been shown to enhance gene expression. See, e.g., Callis et al. (1987) *Genes Develop.* 1:1183-1200.

Likewise, a number of non-translated leader sequences derived from viruses also are known to enhance gene expression. Specifically, leader sequences from Tobacco Mosaic Virus (TMV, the "W-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al.

(1990) *Plant Mol. Biol.* 15:65-79). Other leader sequences known in the art include, but are not limited to, picornavirus leaders such as an Encephalomyocarditis (EMCV) 5' noncoding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154: 9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RNA* 237-256); and MCMV leader (Lommel et al. (1991) *Virology* 81:382-385). See also, Della-Cioppa et al. (1987) *Plant Physiol.* 84:965-968.

Once the coding sequence for the xylanase enzyme is cloned into the expression cassette, it can be transformed into, for example, a plant, plant part or plant host cell. As used herein, "plant" means any plant, particularly a seed plant, and "plant host cell" is a structural and physiological unit of the plant, which comprises a cell wall and also may refer to a protoplast. The plant host cell can be in form of an isolated single cell or can be a cultured cell or can be a part of a higher-organized unit such as, for example, a plant tissue or a plant organ. As used herein, "transformation" means a transfer of a nucleic acid molecule or fragment into the genome of a host cell, resulting in genetically stable inheritance. Host cells containing the transformed nucleic acid molecules or fragments are referred to as "transgenic" cells, and organisms comprising transgenic cells are referred to as "transgenic organisms."

Examples of methods of transforming plants, plant parts and plant host cells include, but are not limited to, *Agrobacterium*-mediated transformation (De Blaere et al. (1987) *Meth. Enzymol.* 153:277-293) and particle bombardment-mediated transformation (Klein et al. (1987) *Nature* 327:70-73; as well as U.S. Pat. No. 4,945,050).

The expression cassette therefore can be introduced into the plant, plant part or plant host cell in any number of ways that are well known in the art. As used herein, "introducing," in the context of a nucleic acid construct such as an expression cassette, means presenting to a plant, plant part or plant host cell a nucleotide sequence encoding the xylanase enzyme as disclosed herein in such a manner that it gains access to the interior of a cell of the plant. Where more than one nucleotide sequence is to be introduced, they can be assembled as part of a single nucleic acid construct, or as separate nucleic acid constructs, and can be located on the same or different nucleic acid constructs.

Accordingly, the nucleotide sequences can be introduced into the host cell of interest in a single transformation event, in separate transformation events, or, for example, in plants, as part of a breeding protocol. The methods of the invention do not depend on a particular method for introducing one or more nucleotide sequences into a plant, only that they gain access to the interior of at least one cell of the plant. Methods for introducing nucleotide sequences into plants are known in the art including, but not limited to, transient transformation methods, stable transformation methods, and virus-mediated methods.

As used herein, "transient transformation" or "transiently transformed" means that a nucleic acid construct such as an expression cassette is introduced into the plant and does not integrate into the genome of the plant.

As used herein, "stable transformation" or "stably transformed" means that a nucleic acid construct such as an expression cassette is introduced into a plant, integrates into the genome of the plant, and is capable of being inherited by the progeny thereof, more particularly, by the progeny of multiple successive generations.

In addition to expression cassettes, numerous plant transformation vectors are well known to one of skill in the art, and the nucleotide sequences described herein can be used in connection with any such vectors. The selection of a vector will depend upon the preferred transformation technique and the target species for transformation. For certain target species, different antibiotic or herbicide selection markers may be preferred as discussed elsewhere herein.

For example, Ti plasmid vectors have been used to deliver foreign DNA, as well as direct DNA uptake, liposomes, electroporation, microinjection and microprojectiles. In addition, bacteria from the genus *Agrobacterium* can be used to transform plant cells. Below are descriptions of representative methods for transforming both monocotyledonous (monocots) and dicotyledonous (dicots) plants, as well as a representative plastid transformation methods.

Many vectors are available for transformation using *Agrobacterium tumefaciens*. These typically carry at least one T-DNA border sequence and include vectors such as pBIN19 (Bevan (1984) *Nucleic Acids Res.* 12: 8711-8721). US Patent Application Publication No. 2006/0260011 describes methods for constructing vectors useful in *Agrobacterium*-mediated transformation.

Transformation without the use of *A. tumefaciens* circumvents the requirement for T-DNA sequences in the chosen transformation vector and consequently vectors lacking these sequences also can be used. Transformation methods that do not rely on *Agrobacterium* include transformation via microinjection, particle bombardment, and protoplast uptake (e.g., PEG and electroporation). As noted above, the choice of vector will depend largely on the preferred selection for the species being transformed.

Methods of transforming monocots are well known in the art and include direct gene transfer into protoplasts using PEG- or electroporation-mediated methods, as well as particle bombardment into callus tissue. Transformation can be undertaken with a single DNA species or multiple DNA species (i.e., co-transformation) and both of these methods are suitable for use herein. Co-transformation may have the advantage of avoiding complete vector construction and of generating transgenic plants with unlinked loci for the gene of interest and the selectable marker, enabling the removal of the selectable marker in subsequent generations, should this be regarded as desirable.

EP Patent Application Nos. 0 292 435 and 0 392 225, as well as Int'l Patent Application Publication No. WO 93/07278, describe methods for preparing callus and protoplasts from an elite inbred line of maize, transformation of protoplasts using PEG or electroporation, and the regeneration of maize plants from transformed protoplasts. See, Fromm et al. (1990) *Bio/Technology* 8:833-844; and Gordon-Kamm et al. (1990) *Plant Cell* 2:603-618, which describe methods for transforming A188-derived maize lines using particle bombardment. Furthermore, Int'l Patent Application Publication No. WO 93/07278 and Koziel et al. (1993) *Biotechnol.* 11:194-200 describe methods for transforming elite inbred lines of maize by particle bombardment. These methods use immature maize embryos of 1.5-2.5 mm length excised from a maize ear 14-15 days after pollination and a PDS-1000He Biolistics device for bombardment. In each case, the transformed cells can be regenerated to whole plants using methods well known in the art.

Methods of transforming dicots also are well known in the art and include *Agrobacterium*-mediated methods as well as methods that do not require *Agrobacterium*. Non-*Agrobacterium*-mediated methods involve the uptake of exogenous genetic material directly by protoplasts or cells. This method can be accomplished by PEG- or electroporation-mediated uptake, particle bombardment-mediated delivery or microinjection. Examples of these methods are described in, for example, Klein et al. (1987) *Nature* 327:70-73; Paszkowski et al. (1984) *EMBO J.* 3:2717-2722; Potrykus et al. (1985) *Mol. Gen. Genet.* 199:169-177; and Reich et al. (1986) *Biotechnology* 4:1001-1004. In each case, the transformed cells can be regenerated to whole plants using methods well known in the art.

*Agrobacterium*-mediated transformation is a preferred method for transforming dicots because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Ukases et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by DNA transformation (Hofgen & Willmitzer (1988) *Nucleic Acids Res.* 16:9877).

Transformation of the target plant species by recombinant *Agrobacterium* usually involves co-cultivation of the *Agrobacterium* with explants from the plant and follows methods well known in the art. Transformed tissue is regenerated on selectable medium carrying the antibiotic or herbicide resistance marker present between the binary plasmid T-DNA borders.

Another method for transforming plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired coding sequence. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) also can be propelled into plant cell tissue.

The plants obtained via transformation with a coding sequence of the interest can be any of a wide variety of plant species, including monocots and dicots; however, the plants used in the method of the invention preferably are selected from the list of agronomically important target crops set forth supra. The expression of a nucleotide sequence of interest in combination with other characteristics important for production and quality can be incorporated into plant lines through breeding. Breeding approaches and methods are known in the art. See, e.g., Welsh, *Fundamentals of Plant Genetics and Breeding* (John Wiley & Sons 1981); *Crop Breeding* (Wood ed., American Society of Agronomy 1983); Mayo, *The Theory of Plant Breeding*, 2" ed. (Clarendon Press 1987); Singh, *Breeding for Resistance to Diseases and Insect Pests* (Springer-Verlag 1986); and Wricke & Weber, *Quantitative Genetics and Selection Plant Breeding* (Walter de Gruyter and Co. 1986).

Whole plants may be regenerated from transgenic cells by methods well known in the art. See, e.g., Fromm et al. (1990), supra; and Gordon-Kamm et al. (1990), supra.

Likewise, the genetic properties engineered into the transgenic seeds and plants described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

The xylanase enzymes also can be incorporated into or maintained in plant lines through breeding or through common genetic engineering technologies. See, id. The relevant methods include, but are not limited to, aneuploid techniques, backcross breeding, dihaploid inbreeding, hybridization, inbreeding, interspecific hybridization, multi-line breeding, variety blend, etc. Hybridization techniques also include the sterilization of plants to yield male or female sterile plants by biochemical, chemical, genetic (including transgenic) or mechanical means.

Compositions of the invention also include non-plant host cells and organisms transformed with a nucleic acid construct encoding the xylanase enzyme, variant or fragment thereof having xylanase activity. As used herein, "host cell" means a cell in which the expression cassette (including a vector comprising the expression cassette) can be propagated and expressed. Host cell also includes any progeny of the subject host cell or its derivatives. It is understood that all progeny may not be identical to the parental cell since there may be mutations that occur during replication; however, such progeny are included within "host cell." Examples of host cells for use herein include, but are not limited to, prokaryotic cells such as bacterial cells, and eukaryotic cells such as fungal (e.g., yeast cells), insect (e.g., *Drosophila* cells) and mammalian cells.

Briefly, methods of expressing a nucleotide sequence in a non-plant host cell or organism includes transforming the host cell or organism with, for example, a nucleic acid construct having a coding sequence for the xylanase enzyme, variant or fragment thereof operably linked to one or more regulatory sequences. The coding sequence for the xylanase enzyme may be the nucleotide sequence set forth in SEQ ID NOs: 5, 7 or 9 or a fragment or variant thereof, or the polypeptide sequence encoding SEQ ID NOs: 6, 8 or 10 or a fragment or variant thereof. Transformed host cells are grown under conditions where the nucleotide sequence is expressed.

Methods for constructing expression cassettes are described above. Once constructed, the expression cassette can be incorporated into a vector to assist in introducing the expression cassette into the host cell.

Methods of introducing nucleic acid constructs such as expression cassettes and vectors into host cells are well known in the art and will vary depending upon the host cell selected. See, e.g., Davis et al., *Basic Methods in Molecular Biology* (Elsevier Press 1986). Examples of methods for introducing nucleic acid constructs such as expression cassettes or vectors into host cells include, but are not limited to, *Agrobacterium*-mediated transformation, calcium-phosphate-mediated transformation, cyclodextrin-mediated transformation, electroporation, liposome-mediated transformation, nanoparticle-mediated transformation, particle bombardment, polymer-mediated transformation, and virus-mediated transduction. See, e.g., Bacchetti & Graham (1977) *Proc. Natl. Acad. Sci. USA* 74:1590-1594; Bertram (2006)

*Current Pharm. Biotechnol.* 7:277-228; Fischer et al. (2002) *Bioconjugate Chem.* 13:1124-1133; Graham & van der Eb (1973) *Virology* 52:456-467; Menuel et al. (2008) *Bioconjugate Chem.* 19:2357-2362; Soltani et al., "Agrobacterium-mediated transformation of non-plant organisms" 649-675 In: *Agrobacterium: From Biology to Biotechnology* (Tzfira & Citovsky eds., Springer 2008); and Tsukakoshi et al. (1984) *Appl. Physics B-Photophys. Laser Chem.* 35:135-140.

As above, the host cell can be transiently transformed or stably transformed.

Examples of non-plant host cells include, but are not limited to, the ethanologenic organisms discussed above, as well as fungi such as yeast, especially *Aureobasidium, Cryptococcus, Kluyveromyces, Rhodotorula, Saccharomyces* and *Sporobolomyces*.

Once the xylanase enzyme, variant or fragment thereof is expressed by the host cell or organism, it can be purified from the host cell or organism for use in the compositions described herein.

The xylanase enzyme can be isolated and formulated into compositions for use in lignocellulose bioprocessing. In this manner, the compositions can be formulated at a high pH typically at pH 8.5 or higher, including, pH 10, pH 11, pH 12 and higher, preferably pH 12. Other components can be included within the composition including, but not limited to, other bioprocessing enzymes or chemicals as well as stabilizers.

Methods

Methods of the invention include contacting lignocellulosic material with an enzyme composition as described herein to hydrolyze the cellulose, hemicellulose and lignin polymers therein into monomers for subsequent use in various feed, food/beverage and technical industries. In particular, the methods find use in high temperature, high pH applications.

Briefly, bioconversion of lignocellulosic materials to useful, higher value products normally requires multi-step processes that can include: (1) pretreatment (e.g., biological, chemical or mechanical) of the lignocellulosic material, and (2) hydrolysis of cellulose, hemicellulose and/or lignin polymers to produce simpler, yet readily metabolizable, molecules (e.g., hexose or pentose sugars) by contacting them with the xylanase enzyme, variant or fragment thereof. Additional steps optionally can be performed, such as may be required in the feed, food/beverage and technical industries. Such additional steps can include: (3) bio-utilization of the molecules to support microbial growth or to produce chemical products, and (4) separation and purification of the chemical products.

Lignocellulose can be found, for example, in the stems, leaves, hulls, husks and cobs of non-woody plants, or leaves, branches and wood of woody plants such as trees. Lignocellulosic material also can be obtained from lignocellulosic waste products, such as plant residue and paper waste. Examples of plant residues include, but are not limited to, stems, leaves, hulls, husks, cobs and the like, as well as wood, wood chips, wood pulp and sawdust. Examples of paper waste include, but are not limited to, discarded photocopy paper, computer printer paper, notebook paper, notepad paper, typewriter paper and the like, as well as discarded newspapers, magazines, cardboard and paper-based packaging materials. Lignocellulosic material also can be from agricultural residues, forestry residues, herbaceous material, municipal solid wastes, and pulp and paper mill residues.

The methods can include a step of pre-treating lignocellulosic material. While the lignocellulosic material can be used "as is," it also can be pretreated with methods well known in the art including biological pretreatment, chemical pretreatment or physical pretreatment. Examples of biological pretreatment include, but are not limited to, use of lignin-solubilizing microorganisms such as *Clostridium* spp. or *Streptomyces* spp. Examples of chemical pretreatment include, but are not limited to, alkaline treatment, ammonia treatment, dilute acid treatment, organic solvent treatment, ozone treatment, sulfur dioxide treatment, carbon dioxide treatment and pH-controlled hydrothermolysis. Examples of physical pretreatment include, but are not limited to, various types of hydrothermolysis, irradiation, milling, steaming/steam explosion and sonicating (ultra-sonicating). See generally, Hsu, "Pretreatment of biomass" 179-212 In: *Handbook on Bioethanol: Production and Utilization* (Wyman ed., Taylor & Francis 1996); Ghosh & Singh (1993) *Adv. Appl. Microbiol.* 39:295-333; McMillan, "Pretreating lignocellulosic biomass: a review" Chapter 15 In: *Enzymatic Conversion of Biomass for Fuels Production* (Himmel et al. eds., American Chemical Society 1994); Gong et al. (1999) *Adv. Biochem. Eng./Biotechnol.* 65:207-241; Olsson & Hahn-Hagerdal (1996) *Enz. Microb. Tech.* 18:312-331; and Vallander & Eriksson (1990) *Adv. Biochem. Eng./Biotechnol.* 42:63-95; as well as U.S. Pat. Nos. 5,733,741 and 6,333,181.

The methods comprise contacting lignocellulosic material having cellulose, hemicellulose and/or lignin with the xylanase enzyme composition to hydrolyze the material to simpler, more readily utilizable molecules. As used herein, "contacting" means bringing together the enzyme, variant or fragment thereof and the lignocellulosic material, thereby facilitating intermolecular interactions necessary to cause the enzyme, variant or fragment to hydrolyze or act upon the lignocellulosic material. Depending upon the source of the enzyme, variant or fragment thereof, contacting can occur in vitro, ex vivo or in vivo.

Generally, a suitable enzyme dosing is about 0.01 units to 1000 units per gram of dry lignocellulosic material, and more preferably 0.1 units to 500 units per gram. The activity of the enzyme composition can be determined as follows: to 0.5 ml of xylan solution (1%; Sigma, St. Louis, Mo.; prepared in a 50 mM phosphate buffer, pH 7) add 0.5 ml of suitably diluted enzyme in the same buffer. The solution can be incubated at 70° C. for about 10 minutes. The reaction then can be stopped by adding 1 ml DNS reagent (3,5-dinitrosalicylate 10 g/L; Na/K tartrate 300 g/L; NaOH 16 g/L), and the color can be developed by boiling the sample for 5 minutes. See, e.g., Ghose (1987), surpa; and Miller (1959), supra. The absorbency then can be measured at a wavelength of 540 nm. One enzyme unit liberates one µmol of reducing sugars calculated as xylose per minute under assay conditions. The activity can be calculated from an enzyme dilution liberating 4 mmol of reducing sugar under assay conditions.

If the activity of the enzyme composition is insufficient, it can be concentrated prior to use. Methods of concentrating polypeptides and proteins such as enzymes are well known in the art. See, e.g., Ahmed, *Principles and Reactions of Protein Extraction, Purification, and Characterization* (CRC Press 2004); Dennison, *A Guide to Protein Isolation*, $2^{nd}$ ed. (Kluwer Academic Publishers 2003); Degerli & Akpinar (2001) *Anal. Biochem.* 297:192-194; and *Protein Methods*, $2^{nd}$ ed. (Bollag et al. eds., Wiley Publishers 1996). For example, a simple ultrafiltration can be used to concentrate a supernatant of the enzyme 5-25 fold.

The contacting time can and will vary depending upon factors such as the result desired, the type of lignocellulosic material used, the amount of lignocellulosic material used, the amount of enzyme used, the specific activity of the enzyme composition, the temperature, the pH, and the like.

This step, however, can be carried out for a time sufficient to decrease the cellulase, hemicellulase and/or lignin content of the lignocellulosic material. As such, the lignocellulosic material and enzyme, variant or fragment thereof can be contacted for about 5 minutes, about 10 minutes, about 15 minutes, about 30 minutes, about 45 minutes, about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, about 48 hours, or more.

As noted above, it is preferred that the contacting be carried out at a temperature and pH that enhances the enzyme's activity in vitro. Temperatures can range from about 10° C. to about 100° C., with about 65° C. to 95° C. being preferred. The preferred pH for this step can be from about pH 6 to about pH 12. It is a characteristic of the enzyme composition described herein that it can be active over a wide pH-range as well as having high activity at pH 6-12, which is the pH required for many processes in the feed, food/beverage and technical industries such as, for example, in the storage towers used by the pulp mills. Because the enzyme is active over a wide pH-range, the pH can be varied during the methods. As noted above, the enzyme has both xylanase activity at about pH 6, and retains both activities even up to about pH 12. Thus, the pH can begin at about pH 6, in which both xylanase activity is present, and then steadily be changed to a more basic pH such as pH 12, in which both activities will continue. Alternatively, the pH can be at about pH 12, and then steadily be changed to a more acidic pH such as pH 6.

The enzyme compositions or modified organisms can be used in various methods. The xylanase enzymes have the advantage that they can be used at high temperatures and high pHs. In one embodiment, the methods can be used in the feed industry to make animal feeds. The methods provide for hydrolyzing xylans in a feed prior to or during consumption by an animal comprising the following steps: (a) obtaining a feed material comprising lignocellulosic material such as cellulose, hemicellulose and lignin; (b) contacting an enzyme composition having a xylanase enzyme (for example, SEQ ID NOs: 6, 8 or 10), or a variant or fragment thereof having xylanase activity, to the feed material in a sufficient amount and for a sufficient time period to cause hydrolysis of xylans, thereby hydrolyzing the xylans in the feed prior to or during consumption by the animal. The methods also can include (c) administering the feed material to the animal, wherein after consumption, the xylanase activity causes hydrolysis of xylans of the feed in the digestive tract of the animal. The feed can be, for example, a cereal, corn, grain, and the like.

In another embodiment, the methods can be used in the food/beverage industry to process fruit or vegetable materials. The methods provide for hydrolyzing xylans in a food or beverage prior to consumption by a human comprising the following steps: (a) providing a fruit or vegetable material comprising lignocellulosic material such as cellulose, hemicellulose and lignin such as fruit or vegetable material; and (b) contacting an enzyme composition having a xylanase enzyme (for example, SEQ ID NOs: 6, 8 or 10), or a variant or fragment thereof having xylanase activity, to the fruit or vegetable material in a sufficient amount and for a sufficient time period to cause hydrolysis of xylans, thereby processing the fruit or vegetable material. The food can be, for example, such a fruit or vegetable juice, beer, wine, syrup, puree or extract and the like.

In another embodiment, the methods can be used in the technical industry to treat pulp. The methods provide for hydrolyzing xylans in non-woody or woody plant materials comprising the following steps: (a) providing a non-woody or woody plant material such as crop, plant and tree biomass comprising cellulose, hemicellulose and lignin; (b) contacting an enzyme composition having a xylanase enzyme (for example, SEQ ID NOs: 6, 8 or 10), or a variant or fragment thereof having xylanase activity, with the non-woody or woody plant material in a sufficient amount and for a sufficient time period to cause hydrolysis of xylans, thereby processing the non-woody or woody plant material. The methods also can include prior to step (b), when bleaching pulpy materials, exposing chemical pulp to a chlorine dioxide bleaching stage to produce a partially bleached pulp; (b) contacting the partially bleached pulp with the enzyme composition comprising the enzyme, variant or fragment thereof having xylanase activity; and (c) exposing the treated pulp to a second chlorine dioxide bleaching without an alkaline extraction stage.

In another embodiment, the methods can be used in the technical industry to produce ethanol. The methods provide for hydrolyzing xylans in non-woody or woody plant materials comprising the following steps: (a) providing a non-woody or woody plant material such as crop, plant or tree biomass comprising cellulose, hemicellulose and lignin; (b) contacting an enzyme composition having a xylanase enzyme (for example, SEQ ID NOs: 6, 8 or 10), or a variant or fragment thereof having xylanase activity, with the non-woody or woody plant material in a sufficient amount and for a sufficient time period to cause hydrolysis of xylans, thereby processing the non-woody or woody plant material for subsequent ethanol production.

In another embodiment, the methods can be used to make biofuels. The methods provide for hydrolyzing xylans in non-woody or woody plant materials comprising the following steps: (a) providing a non-woody or woody plant material such as crop, plant or tree biomass comprising cellulose, hemicellulose and lignin; (b) contacting an enzyme composition having a xylanase enzyme (for example, SEQ ID NOs: 6, 8 or 10), or a variant or fragment thereof having xylanase activity, with the non-woody or woody plant material in a sufficient amount and for a sufficient time period to cause hydrolysis of xylans, thereby processing the non-woody or woody plant material for subsequent biofuel production.

EXPERIMENTAL

The following examples are offered for purposes of illustration, not limitation.

Example 1

Xylanases Having Thermostable and Alkaliphilic Xylanase Activity

This example shows xylanases can have thermostable and alkaliphilic xylanase activity.

Xylanase polypeptides were produced using recombinant *E. coli* as a host. Selected nucleotide sequences encoding for xylanases were cloned into a pET24a *E. coli* expression vector using restriction enzyme sites that placed the nucleotide sequence in-frame downstream of an inducible T7lac promoter. Such nucleotide sequences included *Bacillus stearothermophilus* xylanase (BsXynA; SEQ ID NO:9) and *Thermotoga maritima* xylanase (TmXynB; SEQ ID NO:7). Nucleotide sequences coding for the specific enzymes were generated by back translating the polypeptide sequence of the enzyme using the codon preference for *E. coli*. Expression vectors were introduced into an *E. coli* expression strain, BL21 Star (DE3; Invitrogen).

Recombinant *E. coli* isolates containing the modified pET24a expression vector were selected on standard LB agar containing 50 ug/ml kanamycin. Isolates were grown with shaking at 37° C. for 8 hours to overnight in 20 ml of LB media containing 50 ug/ml kanamycin.

20 ml of *E. coli* culture was transferred to 1 L of autoinduction medium (9.57 g trypton, 4.8 g yeast extract, 2 ml of 1 M $MgSO_4$, 1 ml of 1000× trace metals, 20 ml of 50× 5052, and 20 ml of 50× M) (1000× trace metals: 36 ml sterile water, 50 ml of 0.1 M $FeCl_3$ in 0.12 M HCl, 2 ml of 1 M $CaCl_2$, 1 ml of 1 M $MnCl_2$ 4 $H_2O$, 1 ml of 1 M $ZnSO_4$ 7 $H_2O$, 1 ml of 0.2 M $CoCl_2$ 6 $H_2O$, 2 ml of 0.1 M $CuCl_2$ 2 $H_2O$, 1 ml of 0.2 M $NiCl_2$ 6 $H_2O$, 2 ml of 0.1 M $Na_2MoO_4$ 2 $H_2O$, and 2 ml of 0.1 M $H_3BO_3$) (50× 5052: 25 g glycerol, 73 ml $H_2O$, 2.5 g glucose, and 10 g α-lactose monohydrate) (50× M: 80 ml $H_2O$, 17.75 g $Na_2HPO_4$, 17.0 g $KH_2PO_4$, 13.4 g $NH_4Cl$, and 3.55 g $Na_2SO_4$) with 25 ug/ml kanamycin, and grown with shaking at 28° C. overnight.

The *E. coli* cells were harvested out of the autoinduction medium by centrifugation at 10,000× g for 15 minutes, and the collected cells were frozen at −80° C. Cells were lysed by re-suspending the cell pellet in a buffer (50 mM Tris, pH 7.5, 50 mM NaCl, 0.1 mM EDTA) containing DNase (1 U/ml buffer) and using a French Press. Insoluble debris was removed by centrifugation at 12,000× g for 20 minutes at 4° C.

For TmXynB (SEQ ID NOs: 7 and 8), the supernatant containing total soluble protein and recombinant enzyme was transferred to a fresh 40 ml centrifuge tube and was incubated at 75° C. for 30 minutes. The xylanases remained soluble and were separated from precipitated protein by centrifugation at 12,000× g for 30 minutes, and the collected proteins were available for further characterization.

For BsXynA (SEQ ID NOs: 9 and 10), the supernatant, following French Press lysis and centrifugation, was poured over an anionic affinity column using ÄKTA™ Fast Protein Liquid Chromatography (FPLC; GE Healthcare Life Sciences; Uppsala, Sweden) and was eluted as fractions using 50 mM Tris, pH 8.0, with a gradient of NaCl from 0 to 2 M.

Purity for all xylanases was determined using SDS-PAGE and densitometry.

Xylanase activity during aqueous ammonia pretreatment was evaluated by combining the xylanase preparations as described above with birchwood substrate-based biomass. The pretreatment cocktail included 0.75% birchwood xylan and varying concentrations of aqueous ammonia. The pH of each treatment was between pH 11.3 and pH 12.4.

The quantity of xylanase enzyme preparation used was determined by a dose response curve, in which various amounts of enzyme were added to an assay performed with 0.75% brichwood xylan and 50 mM Tris, pH 8.0, and incubated for 1 hour. The optimal amount of xylanase was determined to be a maximal amount that did not saturate the birchwood xylan substrate. These amounts were 0.6 μg per mg of xylan for BsXynA (SEQ ID NO:10) and 0.25 μg per mg of xylan for TmXynB (SEQ ID NO:8).

The pretreatment cocktail contained 0.75% birchwood xylan, xylanase enzyme preparation and aqueous ammonia. The pretreatment cocktail was incubated at various temperatures for 1 hour prior to measuring xylanase activity for BsXynA (SEQ ID NO:10) and TmXynB (SEQ ID NO:8) by the DNS colorimetric assay as described below under the heading "xylanase assay".

Xylanase Assay:

cells were centrifuged at 8000×g for 5 minutes. The supernatant was discarded, and cells were re-suspended at $OD_{600\ nm}$=200 in a 0.1 M glycine buffer at pH 12 containing 7% $NH_4OH$. 100 μl of re-suspended cells were incubated for 1 hour at 60° C. After the 1 hour incubation, 200 μl of a 5% w/v oat spelt xylan (Sigma) solution prepared in the glycine buffer at pH 12 was added as a substrate, and the reaction was allowed to proceed for 1 hour at 60° C. After the 1 hour incubation, enzymatic activity was detected with the DNS colorimetric assay for reducing sugars as described in Miller (1959), supra.

The DNS assay was used to measure production of reducing ends of the xylose polysaccharides generated by the xylanases; thus, this method measured xylanase activity. As noted above, the assay is based on the reaction of the reducing ends with DNS; the product produced can be measured colorimetrically using spectrometry. See, e.g., Miller (1959), supra. The colorimetric values were translated into a reducing sugar concentration via a standard curve, in which the absorbance at A540 was determined for a range of 0-10 mM xylose.

Xylanase activity was also evaluated after exposing the enzyme preparations to pretreatment in aqueous ammonia to determine to what extent the enzymes were irreversibly altered by the pretreatment conditions. To determine the stability of the *E. coli*-produced xylanases, the xylanase enzyme preparations described above were incubated in varying concentrations of aqueous ammonia at 60° C., followed by neutralization and subsequent analysis of xylanase activity. As an additional control, analysis also was performed with M1 xylanase (Megazyme Int'l Ireland Ltd.), which is from *Trichoderma viride*. The same amounts of xylanase enzyme preparation were used in these assays as in those described above; M1 was used at 1 μg per mg of xylan.

The pretreatment was performed by incubating the xylanases in the presence of birchwood xylan substrate at 60° C. in varying concentrations of aqueous ammonia. A control sample was neutralized immediately (AAPT 0 hour), while test samples were incubated in the aqueous ammonia for 1 hour. The samples were neutralized by incubating with Dowex™ Weak Acid Resin (Dow Chemical Co.; Midland, Mich.) plus additional birchwood xylan for either 0 hour (ACT 0 hour control) or for 1 hour (ACT 1 hour test samples). Xylanase activity was determined by the DNS assay as described above.

Tables 1 and 2 show the relative xylanase activity of each enzyme during an aqueous ammonia pretreatment. Values were calculated as a percentage of the enzyme activity observed at 60° C. and 0.01% aqueous ammonia which was set to 100%.

TABLE 1

BsXynA (SEQ ID NO: 10) Xylanase Activity During Aqueous Ammonia Pretreatment.

| Percentage of aqueous ammonia | 50° C. | 60° C. | 80° C. |
| --- | --- | --- | --- |
| 0.01 | 53.5 | 100.0 | 34.9 |
| 0.1 | 34.3 | 77.6 | 5.6 |
| 1 | 31.5 | 50.8 | 0.0 |
| 4 | 20.6 | 15.7 | 0.0 |
| 8 | 8.0 | 0.4 | 0.0 |

TABLE 2

TmXynB (SEQ ID NO: 8) Xylanase Activity During Aqueous Ammonia Pretreatment.

| Percentage of aqueous ammonia | 50° C. | 60° C. | 80° C. |
|---|---|---|---|
| 0.01 | 29.7 | 100.0 | 193.2 |
| 0.1 | 16.5 | 74.1 | 141.8 |
| 1 | 19.6 | 42.2 | 4.5 |
| 4 | 9.4 | 27.0 | 3.6 |
| 8 | 3.5 | 4.7 | 3.5 |

The xylanases therefore are active during an aqueous ammonia pretreatment. During the incubation in aqueous ammonia, the xylanases were able to hydrolyze the birchwood xylan substrate, suggesting that these enzymes may be used during the pretreatment of cellulosic biomass to convert the biomass to fermentable sugars. The various enzymes analyzed showed some differences in tolerance to increasing concentrations of aqueous ammonia and tolerance to higher temperatures.

Sensitivity of the enzymes to temperature while increasing the concentration of aqueous ammonia will be important to consider when selecting an appropriate xylanase for pretreatment of cellulosic biomass.

Tables 3 to 5 show that the various xylanases retain xylanase activity after incubation in ammonia-based pretreatment conditions with a biomass substrate present.

TABLE 3

M1 Xylanase Activity (mM xylose equivalents) with Aqueous Ammonia Pretreatment (AAPT) Followed by Neutralization and an Hour Activity Incubation (AI).

| Percentage of aqueous ammonia | AAPT: 0 hr, AI: 0 hr | AAPT: 0 hr, AI: 1 hr | AAPT: 1 hr, AI: 0 hr | AAPT: 1 hr, AI: 1 hr |
|---|---|---|---|---|
| 0.01 | 37.8 | 100.0 | 18.2 | 19.3 |
| 1 | 72.7 | 129.7 | 10.8 | 9.6 |
| 4 | 56.1 | 107.1 | 7.3 | 6.2 |
| 8 | 51.7 | 97.1 | 5.4 | 5.3 |

Expressed as percentage, where 100% = activity at 0.01% AA, AAPT: 0 hr, Act: 1 hr.

TABLE 4

BsXynA (SEQ ID NO: 10) Xylanase Activity (mM xylose equivalents) with Aqueous Ammonia Pretreatment (AAPT) Followed by Neutralization and an Hour Activity Incubation (AI).

| Percentage of aqueous ammonia | AAPT: 0 hr, AI: 0 hr | AAPT: 0 hr, AI: 1 hr | AAPT: 1 hr, AI: 0 hr | AAPT: 1 hr, AI: 1 hr |
|---|---|---|---|---|
| 0.01 | 3.6 | 100.0 | 56.7 | 187.1 |
| 1 | 3.8 | 82.6 | 20.1 | 65.1 |
| 4 | 3.1 | 70.4 | 3.6 | 3.7 |
| 8 | 2.4 | 75.0 | 2.4 | 4.7 |

Expressed as percentage, where 100% = activity at 0.01% AA, AAPT: 0 hr, Act: 1 hr.

TABLE 5

TmXynB (SEQ ID NO: 8) Xylanase Activity (mM xylose equivalents) with Aqueous Ammonia Pretreatment (AAPT) Followed by Neutralization and an Hour Activity Incubation (AI).

| Percentage of aqueous ammonia | AAPT: 0 hr, AI: 0 hr | AAPT: 0 hr, AI: 1 hr | AAPT: 1 hr, AI: 0 hr | AAPT: 1 hr, AI: 1 hr |
|---|---|---|---|---|
| 0.01 | 4.0 | 100.0 | 31.2 | 136.5 |
| 1 | 3.4 | 91.6 | 18.3 | 107.7 |
| 4 | 2.5 | 84.1 | 8.3 | 68.8 |
| 8 | 2.8 | 92.3 | 2.7 | 12.3 |

Expressed as percentage, where 100% = activity at 0.01% AA, AAPT: 0 hr, Act: 1 hr.

Some of the enzymes therefore can be used during ammonia-based pretreatments and continue to function after pretreatment of biomass during the cellulosic conversion of biomass to fermentable sugars process. The M1 enzyme (control) showed little to no tolerance to exposure to an ammonia-based pretreatment, while BsXynA (SEQ ID NO: 10) and TmXynB (SEQ ID NO:8) both showed varying levels of tolerance to the ammonia-based pretreatment. These xylanases may be enzymes of choice when considering the development of a cellulosic biomass conversion process that includes the use of enzymes capable of breaking down biomass.

Example 2

Xylanase 10 Protein and Effect on Plant Leaf Tissue

Previous experience with transgenic plants expressing xylanase enzymes from the xylanase family 11 class of enzymes has resulted in the association of negative agronomic phenotypes with the expression of family 11 xylanase enzymes. Transgenic plants expressing family 11 xylanase enzymes where the enzyme is expressed in the seed of the plant frequently display negative seed phenotypes such as shriveled seeds. In addition, infiltrating plant leaves with a semi-purified xylanase family 11 enzyme resulted in necrotic leaf lesions. There is a need in the art for xylanase enzymes which can be expressed in transgenic plants without associated negative phenotypes such as necrotic lesions or shriveled seed. The following example describes plant phenotypes associated with the presence of family 10 endo 1, 4 beta xylanase enzymes in the leaf of the plant.

Xylanase family 10 enzyme preparations were tested for the ability to elicit a plant necrotic phenotype by infiltrating plant leaves (tobacco and corn) with semi-purified enzyme preparations. The plants were observed for the development of necrotic lesions. It was noted that none of the family 10 xylanase enzymes tested were associated with necrotic lesions in plant leaves when the enzyme was infiltrated into the leaf.

Four polynucleotide sequences encoding family 10 endo 1, 4 beta xylanase polypeptides were cloned into the expression vector pET24 (Novagen). The four nucleotide sequences were TmXynA (Genbank ID NO: AAD35155; SEQ ID NO:5), TmXynB (Genbank ID NO: AAD35164; SEQ ID NO:7), CtXynZ holo enzyme (Genbank ID NO: ABN53181; SEQ ID NO:1) and a fragment of CtXynZ which contains ferrulic acid esterase activity (SEQ ID NO:3). In each of the recombinant pET24 expression vectors, a stop codon was introduced before the His-tag which is a component of the pET24 expression vector. This stop codon ensured that the polypeptides produced by the recombinant pET 24 expression vectors would not contain a His tag.

The recombinant pET24 expression vectors (containing polynucleotide sequence that encodes for a xylanase 10 protein) were transformed into the *E. coli* host BL21[DE3] using standard molecular biology techniques. In order to purify the protein from the recombinant *E. coli* host, the recombinant BL21 cells were grown in 50 mL of autoinduction media (9.57 g trypton, 4.8 g yeast extract, 2 ml of 1 M MgSO4, 1 mL of 1000× trace metals, 20 ml of 50× 5052, 20 mL of 50× M) (1000× trace metals: 36 mL sterile water, 50 mL of 0.1M FeCl3 in 0.12M HCl, 2 mL of 1M CaCl2, 1 mL of 1M MnCl2 4 H20, 1 mL of 1M ZnSO4 7 H20, 1 mL of 0.2M CoCl2 6 H20, 2 mL of 0.1M CuCl2 2 H20, 1 mL of 0.2M NiCl2 6 H20, 2 mL of 0.1M Na2MoO4 2 H20, 2 mL of 0.1M H3BO3) (50×5052: 25 g glycerol, 73 mL H20, 2.5 g glucose 10 g alpha-lactose monohydrate) (50× M: 80 mL H20, 17.75 g Na2HPO4, 17.0 g KH2PO4, 13.4 g NH4Cl, 3.55 g Na2SO4)) also containing 25 ug/mL kanamycin as a selection agent for the recombinant pET24 plasmid. The bacterial cells were recovered from the 50 mL of culture by centrifugation and then resuspended in buffer without protease inhibitor (50 mM Tris pH 7.5, 50 mM NaCl, 0.1 mM EDTA). The resuspended cells were lysed by passing this solution through a French press and the cellular debris was removed by centrifugation (discard the pellet, retain the supernatant). The supernatant was further heat treated by incubating at 70 degrees C. for 30 minutes and the resulting denatured proteins were removed by centrifugation (discard the pellet, retain the supernatant). The supernatant was further concentrated and de-salted by passing through a sephadex G-25 medium-sized matrix column (GE Healthcare, catalog #17-0851-01) and eluting the bound protein into the buffer 10 mM potassium phosphate buffer pH 5.8.

The protein in the above described preparations were quantified by the standard Bradford Assay using bovine gamma globulin (Pierce) to generate the standard curve. The purity of the xylanase enzyme preparations described above was determined by performing SDS-PAGE with Coomassie staining of the proteins, followed by densitometry using a BioRad Imager with the Quantity One software package, version 4.6.3 (Quantity One 1-D Analysis Software, Catalog #: 170-9600, Version 4.6.5, Build 094) The CtXynZ protein (Genbank ID NO: ABN53181; SEQ ID NO:2) was 41.2 percent pure, TmXynA (Genbank ID NO: AAD35155; SEQ ID NO:6) was 78 percent pure and TmXynB (Genbank ID NO: AAD35164; SEQ ID NO:8) was 96 percent pure. In addition, xylanase enzyme activity was demonstrated by the waxy activity assay essentially as described below; however, the standards used for this assay were 0, 20, 40, 60, 80 and 100 mM xylose and the assay was allowed to progress for 4 hours. All of the enzyme preparations contained xylanase enzyme activity based upon the waxy activity assay except for the negative control of CtXynA FAE component only (SEQ ID NO:4).

The xylanase enzyme preparations were infiltrated into the leaves from tobacco or corn to determine if the xylanase 10 enzyme would elicit a necrotic phenotype in plant tissue. Tobacco leaves from transgenic TEV-B tobacco plants (made in the tobacco cultivar Xanthi) containing a mutated P1/HC-Pro gene from TEV that suppresses post-transcriptional gene silencing (Mallory et al., Nat Biotechnol 20:622 (2002)) were used for transient expression of selected enzymes. Infiltration of individual leaves was carried out on corn (about 3 weeks old) and TEV-B tobacco plants (about 4 weeks old) using a 5 mL syringe by pressing the tip of the syringe (without a needle) against the abaxial surface of the leaf. Plants were infiltrated with two different doses of xylanase enzyme preparation, either 150 ug/mL or 25 ug/mL; the wheat arabinoxylan control was infiltrated at 1 mg/ml or 0.1 mg/ml while the digested wheat arabinoxylan was infiltrated at 10 mM or 1 mM. Infiltrated plants were maintained at 22-25 degrees C. with a photoperiod of 16 hours light and 8 hours dark. Plant tissue was harvested after 7 days post infiltration for subsequent analysis.

Leaves from both tobacco plants and corn plants infiltrated with xylanase 10 protein were analyzed for visual symptoms such as necrotic lesions demonstrated by wilting and browning of the leaf tissue. None of the xylanase 10 protein infiltrated tissues developed necrosis or lesions; preparations included CtXynA holoenzyme (SEQ ID NO:2), CtXynA FAE component (SEQ ID NO: 4), TmXynA (SEQ ID NO:6), and TmXynB (SEQ ID NO:8). As a negative control, the substrate wheat arabinoxylan was infiltrated into tobacco and corn leaves essentially as described above for infiltrating xylanase 10 protein. A digested wheat arabinoxylan prep was also infiltrated to determine if xylanase breakdown products induce a plant phenotype. The wheat arabinoxylan did not induce plant phenotypes; however, the digested wheat arabinoxylan preparation did induce necrotic lesions in both tobacco and corn leaves. As pure speculation, it is possible that the M1 xylanase that was used to digeset the wheat arabinoxylan was not properly filtered out from the breakdown products and was responsible for causing necrosis in the infiltration tobacco and corn leaves. M1 xylanase has induced lesions when infiltrated into tobacco or corn leaves.

In addition, extracts from plants leaves infiltrated with the xylanase 10 enzyme preparations were assayed using the waxy activity assay to determine if the infiltrated xylanase preparation retained xylanase activity. All of the xylanase preparations infiltrated into plant leaves contained xylanase enzyme activity except for the negative control CtXynA FAE component only (SEQ ID NO:4) which does not have xylanase activity.

Waxy Activity Assay:

10 uL of enzyme preparation were incubated with 50 uL of wheat arabinoxylan (prepared as described by Megazyme). Standards were generated by combining 50 uL of arabinoxylan with 10 uL of xylose standard. These preparations were incubated for 3 hours at 40 degrees C. without agitation. The reactions were quantified by adding 50 uL of DNS (dissolve 5.0 g of 3,5-dinitrosalicylic acid and 150 g sodium potassium tartrate tetrahydrate in 900 mL of 0.4 M sodium hydroxide. Transfer to 1 L volumetric flask and adjust volume to 1 L with 0.4 M sodium hydroxide) and incubating for 10 minutes at 95 degrees C. The absorbance at 540 nM of the resulting preparations were determined. The xylose standards were used to establish a standard curve and the absorbance readings from the xylanase enzyme preparations were calculated based upon the standard curve.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A host cell stably transformed with a nucleic acid construct comprising a promoter operably linked to a nucleotide sequence selected from the group consisting of SEQ ID NOs: 5 and 9, wherein the cell is a bacterial cell, fungal cell, insect cell, mammalian cell or plant cell, and wherein the promoter is heterologous with respect to the nucleotide sequence.

* * * * *

SEQUENCE LISTING

<160> NUMBER OF SEQ ID NOS: 12

<210> SEQ ID NO 1
<211> LENGTH: 2427
<212> TYPE: DNA
<213> ORGANISM: Clostridium thermocellum
<220> FEATURE:
<221> NAME/KEY: CDS
<222> LOCATION: (1)..(2427)
<223> OTHER INFORMATION: xylanase Z from C. thermocellum - holo enzyme

<400> SEQUENCE: 1

| | | | | | | | | | | | | | | | | |
|---|---|---|---|---|---|---|---|---|---|---|---|---|---|---|---|---|
| atg | agc | ctg | ccg | aca | atg | cct | ccg | agc | ggt | tat | gat | cag | gtt | cgt | aat | 48 |
| Met | Ser | Leu | Pro | Thr | Met | Pro | Pro | Ser | Gly | Tyr | Asp | Gln | Val | Arg | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggt | gtt | ccg | cgt | ggt | cag | gtt | gtt | aat | att | agc | tat | ttt | agc | acc | gcc | 96 |
| Gly | Val | Pro | Arg | Gly | Gln | Val | Val | Asn | Ile | Ser | Tyr | Phe | Ser | Thr | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | aat | agc | acc | cgt | ccg | gca | cgt | gtt | tat | ctg | cct | ccg | ggt | tat | agc | 144 |
| Thr | Asn | Ser | Thr | Arg | Pro | Ala | Arg | Val | Tyr | Leu | Pro | Pro | Gly | Tyr | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| aaa | gat | aaa | aaa | tat | agc | gtg | ctg | tat | ctg | ctg | cat | ggt | att | ggt | ggt | 192 |
| Lys | Asp | Lys | Lys | Tyr | Ser | Val | Leu | Tyr | Leu | Leu | His | Gly | Ile | Gly | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| agc | gaa | aat | gat | tgg | ttt | gaa | ggt | ggt | ggt | cgt | gca | aat | gtt | att | gcc | 240 |
| Ser | Glu | Asn | Asp | Trp | Phe | Glu | Gly | Gly | Gly | Arg | Ala | Asn | Val | Ile | Ala | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gat | aat | ctg | att | gcc | gaa | ggc | aaa | atc | aaa | ccg | ctg | att | att | gtt | acc | 288 |
| Asp | Asn | Leu | Ile | Ala | Glu | Gly | Lys | Ile | Lys | Pro | Leu | Ile | Ile | Val | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| ccg | aat | acc | aat | gca | gcc | ggt | ccg | ggt | att | gca | gat | ggc | tat | gaa | aat | 336 |
| Pro | Asn | Thr | Asn | Ala | Ala | Gly | Pro | Gly | Ile | Ala | Asp | Gly | Tyr | Glu | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| ttt | acc | aaa | gat | ctg | ctg | aat | agc | ctg | att | ccg | tat | att | gaa | agc | aat | 384 |
| Phe | Thr | Lys | Asp | Leu | Leu | Asn | Ser | Leu | Ile | Pro | Tyr | Ile | Glu | Ser | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| tat | agc | gtg | tat | acc | gat | cgc | gaa | cat | cgt | gca | att | gcc | ggt | ctg | agc | 432 |
| Tyr | Ser | Val | Tyr | Thr | Asp | Arg | Glu | His | Arg | Ala | Ile | Ala | Gly | Leu | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | ggt | ggt | ggt | cag | agc | ttt | aat | att | ggc | ctg | acc | aat | ctg | gat | aaa | 480 |
| Met | Gly | Gly | Gly | Gln | Ser | Phe | Asn | Ile | Gly | Leu | Thr | Asn | Leu | Asp | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttt | gcc | tat | atc | ggt | ccg | att | agc | gca | gca | ccg | aat | acc | tat | ccg | aat | 528 |
| Phe | Ala | Tyr | Ile | Gly | Pro | Ile | Ser | Ala | Ala | Pro | Asn | Thr | Tyr | Pro | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | cgt | ctg | ttt | ccg | gat | ggt | ggt | aaa | gca | gca | cgt | gaa | aaa | ctg | aaa | 576 |
| Glu | Arg | Leu | Phe | Pro | Asp | Gly | Gly | Lys | Ala | Ala | Arg | Glu | Lys | Leu | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | ctg | ttt | att | gca | tgt | ggc | acc | aat | gat | agc | ctg | att | ggt | ttt | ggt | 624 |
| Leu | Leu | Phe | Ile | Ala | Cys | Gly | Thr | Asn | Asp | Ser | Leu | Ile | Gly | Phe | Gly | |
| | | | | 195 | | | | | 200 | | | | | 205 | | |

| | | | | | | | | | | | | | | | | |
|---|---|---|---|---|---|---|---|---|---|---|---|---|---|---|---|---|
| cag | cgt | gtg | cac | gaa | tat | tgc | gtg | gcc | aat | aat | att | aat | cat | gtg | tat | 672 |
| Gln | Arg | Val | His | Glu | Tyr | Cys | Val | Ala | Asn | Asn | Ile | Asn | His | Val | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| tgg | ctg | att | cag | ggt | ggt | ggc | cat | gat | ttt | aat | gtt | tgg | aaa | ccg | ggt | 720 |
| Trp | Leu | Ile | Gln | Gly | Gly | Gly | His | Asp | Phe | Asn | Val | Trp | Lys | Pro | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctg | tgg | aat | ttt | ctg | cag | atg | gca | gat | gaa | gcc | ggt | ctg | acc | cgt | gat | 768 |
| Leu | Trp | Asn | Phe | Leu | Gln | Met | Ala | Asp | Glu | Ala | Gly | Leu | Thr | Arg | Asp | |
| | | | | 245 | | | | | 250 | | | | | 255 | | |

-continued

| | | |
|---|---|---|
| ggt aat aca ccg gtt ccg acc ccg tca ccg aaa ccg gca aat acc cgt<br>Gly Asn Thr Pro Val Pro Thr Pro Ser Pro Lys Pro Ala Asn Thr Arg<br>260                        265                  270 | 816 |
| att gaa gcc gaa gat tat gat ggc att aat agc agc agc att gaa att<br>Ile Glu Ala Glu Asp Tyr Asp Gly Ile Asn Ser Ser Ser Ile Glu Ile<br>275                   280                   285 | 864 |
| att ggt gtt ccg cct gaa ggt ggt cgt ggt att ggt tat att acc agc<br>Ile Gly Val Pro Pro Glu Gly Gly Arg Gly Ile Gly Tyr Ile Thr Ser<br>290                       295                   300 | 912 |
| ggt gat tat ctg gtg tat aaa agc att gat ttt ggc aat ggt gcg acc<br>Gly Asp Tyr Leu Val Tyr Lys Ser Ile Asp Phe Gly Asn Gly Ala Thr<br>305                   310                   315                   320 | 960 |
| agc ttt aaa gca aaa gtg gcc aat gca aat acc agc aat att gaa ctg<br>Ser Phe Lys Ala Lys Val Ala Asn Ala Asn Thr Ser Asn Ile Glu Leu<br>                   325                   330                   335 | 1008 |
| cgt ctg aat ggt ccg aat ggc acc ctg att ggc acc ctg agc gtt aaa<br>Arg Leu Asn Gly Pro Asn Gly Thr Leu Ile Gly Thr Leu Ser Val Lys<br>                340                   345                   350 | 1056 |
| agc acc ggt gat tgg aat acc tat gaa gaa cag acc tgt agc att agc<br>Ser Thr Gly Asp Trp Asn Thr Tyr Glu Glu Gln Thr Cys Ser Ile Ser<br>355                   360                   365 | 1104 |
| aaa gtg acc ggc att aat gat ctg tat ctg gtg ttt aaa ggt ccg gtg<br>Lys Val Thr Gly Ile Asn Asp Leu Tyr Leu Val Phe Lys Gly Pro Val<br>370                   375                   380 | 1152 |
| aat att gat tgg ttt acc ttt ggt gtt gaa agc agc agc acc ggt ctg<br>Asn Ile Asp Trp Phe Thr Phe Gly Val Glu Ser Ser Ser Thr Gly Leu<br>385                   390                   395                   400 | 1200 |
| ggt gat ctg aat ggt gat ggc aat att aat agc agt gat ctg cag gca<br>Gly Asp Leu Asn Gly Asp Gly Asn Ile Asn Ser Ser Asp Leu Gln Ala<br>                   405                   410                   415 | 1248 |
| ctg aaa cgt cat ctg ctg ggt att tct ccg ctg acc ggt gaa gca ctg<br>Leu Lys Arg His Leu Leu Gly Ile Ser Pro Leu Thr Gly Glu Ala Leu<br>                   420                   425                   430 | 1296 |
| ctg cgt gca gat gtt aat cgt agc ggt aaa gtt gat agc acc gat tat<br>Leu Arg Ala Asp Val Asn Arg Ser Gly Lys Val Asp Ser Thr Asp Tyr<br>435                   440                   445 | 1344 |
| tct gtg ctg aaa cgc tat att ctg cgc att att acc gaa ttt ccg ggt<br>Ser Val Leu Lys Arg Tyr Ile Leu Arg Ile Ile Thr Glu Phe Pro Gly<br>450                   455                   460 | 1392 |
| cag ggt gat gtt cag acc ccg aat ccg agc gtt acc ccg aca cag aca<br>Gln Gly Asp Val Gln Thr Pro Asn Pro Ser Val Thr Pro Thr Gln Thr<br>465                   470                   475                   480 | 1440 |
| ccg att ccg acc att agc ggt aat gca ctg cgt gat tat gcc gaa gca<br>Pro Ile Pro Thr Ile Ser Gly Asn Ala Leu Arg Asp Tyr Ala Glu Ala<br>                   485                   490                   495 | 1488 |
| cgt ggt att aaa att ggc acc tgt gtg aat tat ccg ttt tat aat aat<br>Arg Gly Ile Lys Ile Gly Thr Cys Val Asn Tyr Pro Phe Tyr Asn Asn<br>                   500                   505                   510 | 1536 |
| agc gat ccg acc tat aat agc att ctg cag cgc gaa ttt agc atg gtt<br>Ser Asp Pro Thr Tyr Asn Ser Ile Leu Gln Arg Glu Phe Ser Met Val<br>515                   520                   525 | 1584 |
| gtg tgc gaa aat gaa atg aaa ttt gat gca ctg caa ccg cgt cag aat<br>Val Cys Glu Asn Glu Met Lys Phe Asp Ala Leu Gln Pro Arg Gln Asn<br>530                   535                   540 | 1632 |
| gtt ttt gat ttt agc aaa ggc gat cag ctg ctg gca ttt gca gaa cgt<br>Val Phe Asp Phe Ser Lys Gly Asp Gln Leu Leu Ala Phe Ala Glu Arg<br>545                   550                   555                   560 | 1680 |
| aat ggt atg cag atg cgt ggt cat acc ctg att tgg cat aat cag aat<br>Asn Gly Met Gln Met Arg Gly His Thr Leu Ile Trp His Asn Gln Asn<br>                   565                   570                   575 | 1728 |

| | | | | | | | | | | | | | | | |
|---|---|---|---|---|---|---|---|---|---|---|---|---|---|---|---|
| ccg | agc | tgg | ctg | acc | aat | ggt | aat | tgg | aat | cgt | gat | agc | ctg | ctg | gca | 1776 |
| Pro | Ser | Trp | Leu | Thr | Asn | Gly | Asn | Trp | Asn | Arg | Asp | Ser | Leu | Leu | Ala | |
| | | | 580 | | | | 585 | | | | 590 | | | | | |
| gtg | atg | aaa | aat | cat | att | acc | acc | gtg | atg | acc | cat | tat | aaa | ggc | aaa | 1824 |
| Val | Met | Lys | Asn | His | Ile | Thr | Thr | Val | Met | Thr | His | Tyr | Lys | Gly | Lys | |
| | | | 595 | | | | 600 | | | | 605 | | | | | |
| att | gtg | gaa | tgg | gat | gtt | gcc | aat | gaa | tgt | atg | gat | gat | agc | ggt | aat | 1872 |
| Ile | Val | Glu | Trp | Asp | Val | Ala | Asn | Glu | Cys | Met | Asp | Asp | Ser | Gly | Asn | |
| 610 | | | | | 615 | | | | | 620 | | | | | | |
| ggt | ctg | cgt | agc | agc | att | tgg | cgt | aat | gtt | att | ggc | cag | gat | tat | ctg | 1920 |
| Gly | Leu | Arg | Ser | Ser | Ile | Trp | Arg | Asn | Val | Ile | Gly | Gln | Asp | Tyr | Leu | |
| 625 | | | | | 630 | | | | | 635 | | | | | 640 | |
| gat | tat | gcc | ttt | cgt | tat | gca | cgt | gaa | gca | gat | ccg | gat | gca | ctg | ctg | 1968 |
| Asp | Tyr | Ala | Phe | Arg | Tyr | Ala | Arg | Glu | Ala | Asp | Pro | Asp | Ala | Leu | Leu | |
| | | | | 645 | | | | | 650 | | | | | 655 | | |
| ttt | tat | aat | gat | tat | aat | att | gaa | gat | ctg | ggt | ccg | aaa | agc | aat | gcc | 2016 |
| Phe | Tyr | Asn | Asp | Tyr | Asn | Ile | Glu | Asp | Leu | Gly | Pro | Lys | Ser | Asn | Ala | |
| | | | 660 | | | | 665 | | | | 670 | | | | | |
| gtg | ttt | aat | atg | att | aaa | agc | atg | aaa | gaa | cgt | ggt | gtt | ccg | att | gat | 2064 |
| Val | Phe | Asn | Met | Ile | Lys | Ser | Met | Lys | Glu | Arg | Gly | Val | Pro | Ile | Asp | |
| | | | 675 | | | | 680 | | | | 685 | | | | | |
| ggt | gtt | ggt | ttt | cag | tgc | cat | ttt | att | aat | ggc | atg | tct | ccg | gaa | tat | 2112 |
| Gly | Val | Gly | Phe | Gln | Cys | His | Phe | Ile | Asn | Gly | Met | Ser | Pro | Glu | Tyr | |
| | | 690 | | | | | 695 | | | | | 700 | | | | |
| ctg | gca | agc | att | gat | cag | aat | atc | aaa | cgc | tat | gcc | gaa | att | ggt | gtg | 2160 |
| Leu | Ala | Ser | Ile | Asp | Gln | Asn | Ile | Lys | Arg | Tyr | Ala | Glu | Ile | Gly | Val | |
| 705 | | | | | 710 | | | | | 715 | | | | | 720 | |
| att | gtg | agc | ttt | acc | gaa | att | gat | att | cgt | att | ccg | cag | agc | gaa | aat | 2208 |
| Ile | Val | Ser | Phe | Thr | Glu | Ile | Asp | Ile | Arg | Ile | Pro | Gln | Ser | Glu | Asn | |
| | | | | 725 | | | | | 730 | | | | | 735 | | |
| ccg | gca | acc | gca | ttt | cag | gtt | cag | gcc | aat | aat | tat | aaa | gaa | ctg | atg | 2256 |
| Pro | Ala | Thr | Ala | Phe | Gln | Val | Gln | Ala | Asn | Asn | Tyr | Lys | Glu | Leu | Met | |
| | | | 740 | | | | | 745 | | | | | 750 | | | |
| aaa | att | tgt | ctg | gcc | aat | ccg | aat | tgt | aat | acc | ttt | gtg | atg | tgg | ggc | 2304 |
| Lys | Ile | Cys | Leu | Ala | Asn | Pro | Asn | Cys | Asn | Thr | Phe | Val | Met | Trp | Gly | |
| | | 755 | | | | | 760 | | | | | 765 | | | | |
| ttt | acc | gat | aaa | tat | acc | tgg | att | ccg | ggt | aca | ttt | ccg | ggt | tat | ggt | 2352 |
| Phe | Thr | Asp | Lys | Tyr | Thr | Trp | Ile | Pro | Gly | Thr | Phe | Pro | Gly | Tyr | Gly | |
| 770 | | | | | 775 | | | | | 780 | | | | | | |
| aat | ccg | ctg | att | tat | gat | agc | aat | tat | aat | ccg | aaa | ccg | gct | tat | aat | 2400 |
| Asn | Pro | Leu | Ile | Tyr | Asp | Ser | Asn | Tyr | Asn | Pro | Lys | Pro | Ala | Tyr | Asn | |
| 785 | | | | | 790 | | | | | 795 | | | | | 800 | |
| gcc | att | aaa | gaa | gcc | ctg | atg | ggc | tat | | | | | | | | 2427 |
| Ala | Ile | Lys | Glu | Ala | Leu | Met | Gly | Tyr | | | | | | | | |
| | | | | 805 | | | | | | | | | | | | |

<210> SEQ ID NO 2
<211> LENGTH: 809
<212> TYPE: PRT
<213> ORGANISM: Clostridium thermocellum

<400> SEQUENCE: 2

Met Ser Leu Pro Thr Met Pro Pro Ser Gly Tyr Asp Gln Val Arg Asn
1               5                   10                  15

Gly Val Pro Arg Gly Gln Val Val Asn Ile Ser Tyr Phe Ser Thr Ala
            20                  25                  30

Thr Asn Ser Thr Arg Pro Ala Arg Val Tyr Leu Pro Pro Gly Tyr Ser
        35                  40                  45

```
Lys Asp Lys Lys Tyr Ser Val Leu Tyr Leu His Gly Ile Gly
    50                  55                  60

Ser Glu Asn Asp Trp Phe Glu Gly Gly Arg Ala Asn Val Ile Ala
65                  70                  75                  80

Asp Asn Leu Ile Ala Glu Gly Lys Ile Lys Pro Leu Ile Ile Val Thr
                85                  90                  95

Pro Asn Thr Asn Ala Ala Gly Pro Gly Ile Ala Asp Gly Tyr Glu Asn
                100                 105                 110

Phe Thr Lys Asp Leu Leu Asn Ser Leu Ile Pro Tyr Ile Glu Ser Asn
            115                 120                 125

Tyr Ser Val Tyr Thr Asp Arg Glu His Arg Ala Ile Ala Gly Leu Ser
    130                 135                 140

Met Gly Gly Gly Gln Ser Phe Asn Ile Gly Leu Thr Asn Leu Asp Lys
145                 150                 155                 160

Phe Ala Tyr Ile Gly Pro Ile Ser Ala Ala Pro Asn Thr Tyr Pro Asn
                165                 170                 175

Glu Arg Leu Phe Pro Asp Gly Gly Lys Ala Ala Arg Glu Lys Leu Lys
            180                 185                 190

Leu Leu Phe Ile Ala Cys Gly Thr Asn Asp Ser Leu Ile Gly Phe Gly
        195                 200                 205

Gln Arg Val His Glu Tyr Cys Val Ala Asn Asn Ile Asn His Val Tyr
    210                 215                 220

Trp Leu Ile Gln Gly Gly His Asp Phe Asn Val Trp Lys Pro Gly
225                 230                 235                 240

Leu Trp Asn Phe Leu Gln Met Ala Asp Glu Ala Gly Leu Thr Arg Asp
                245                 250                 255

Gly Asn Thr Pro Val Pro Thr Pro Ser Pro Lys Pro Ala Asn Thr Arg
            260                 265                 270

Ile Glu Ala Glu Asp Tyr Asp Gly Ile Asn Ser Ser Ile Glu Ile
    275                 280                 285

Ile Gly Val Pro Pro Glu Gly Gly Arg Gly Ile Gly Tyr Ile Thr Ser
    290                 295                 300

Gly Asp Tyr Leu Val Tyr Lys Ser Ile Asp Phe Gly Asn Gly Ala Thr
305                 310                 315                 320

Ser Phe Lys Ala Lys Val Ala Asn Ala Asn Thr Ser Asn Ile Glu Leu
            325                 330                 335

Arg Leu Asn Gly Pro Asn Gly Thr Leu Ile Gly Thr Leu Ser Val Lys
            340                 345                 350

Ser Thr Gly Asp Trp Asn Thr Tyr Glu Glu Gln Thr Cys Ser Ile Ser
    355                 360                 365

Lys Val Thr Gly Ile Asn Asp Leu Tyr Leu Val Phe Lys Gly Pro Val
    370                 375                 380

Asn Ile Asp Trp Phe Thr Phe Gly Val Glu Ser Ser Thr Gly Leu
385                 390                 395                 400

Gly Asp Leu Asn Gly Asp Asn Ile Asn Ser Ser Asp Leu Gln Ala
                405                 410                 415

Leu Lys Arg His Leu Leu Gly Ile Ser Pro Leu Thr Gly Glu Ala Leu
            420                 425                 430

Leu Arg Ala Asp Val Asn Arg Ser Gly Lys Val Asp Ser Thr Asp Tyr
            435                 440                 445

Ser Val Leu Lys Arg Tyr Ile Leu Arg Ile Ile Thr Glu Phe Pro Gly
    450                 455                 460
```

Gln Gly Asp Val Gln Thr Pro Asn Pro Ser Val Thr Pro Thr Gln Thr
465                 470                 475                 480

Pro Ile Pro Thr Ile Ser Gly Asn Ala Leu Arg Asp Tyr Ala Glu Ala
            485                 490                 495

Arg Gly Ile Lys Ile Gly Thr Cys Val Asn Tyr Pro Phe Tyr Asn Asn
            500                 505                 510

Ser Asp Pro Thr Tyr Asn Ser Ile Leu Gln Arg Glu Phe Ser Met Val
            515                 520                 525

Val Cys Glu Asn Glu Met Lys Phe Asp Ala Leu Gln Pro Arg Gln Asn
        530                 535                 540

Val Phe Asp Phe Ser Lys Gly Asp Gln Leu Leu Ala Phe Ala Glu Arg
545                 550                 555                 560

Asn Gly Met Gln Met Arg Gly His Thr Leu Ile Trp His Asn Gln Asn
                565                 570                 575

Pro Ser Trp Leu Thr Asn Gly Asn Trp Asn Arg Asp Ser Leu Leu Ala
            580                 585                 590

Val Met Lys Asn His Ile Thr Thr Val Met Thr His Tyr Lys Gly Lys
            595                 600                 605

Ile Val Glu Trp Asp Val Ala Asn Glu Cys Met Asp Asp Ser Gly Asn
610                 615                 620

Gly Leu Arg Ser Ser Ile Trp Arg Asn Val Ile Gly Gln Asp Tyr Leu
625                 630                 635                 640

Asp Tyr Ala Phe Arg Tyr Ala Arg Glu Ala Asp Pro Asp Ala Leu Leu
                645                 650                 655

Phe Tyr Asn Asp Tyr Asn Ile Glu Asp Leu Gly Pro Lys Ser Asn Ala
                660                 665                 670

Val Phe Asn Met Ile Lys Ser Met Lys Glu Arg Gly Val Pro Ile Asp
            675                 680                 685

Gly Val Gly Phe Gln Cys His Phe Ile Asn Gly Met Ser Pro Glu Tyr
            690                 695                 700

Leu Ala Ser Ile Asp Gln Asn Ile Lys Arg Tyr Ala Glu Ile Gly Val
705                 710                 715                 720

Ile Val Ser Phe Thr Glu Ile Asp Ile Arg Ile Pro Gln Ser Glu Asn
                725                 730                 735

Pro Ala Thr Ala Phe Gln Val Gln Ala Asn Asn Tyr Lys Glu Leu Met
                740                 745                 750

Lys Ile Cys Leu Ala Asn Pro Asn Cys Asn Thr Phe Val Met Trp Gly
            755                 760                 765

Phe Thr Asp Lys Tyr Thr Trp Ile Pro Gly Thr Phe Pro Gly Tyr Gly
770                 775                 780

Asn Pro Leu Ile Tyr Asp Ser Asn Tyr Asn Pro Lys Pro Ala Tyr Asn
785                 790                 795                 800

Ala Ile Lys Glu Ala Leu Met Gly Tyr
                805

<210> SEQ ID NO 3
<211> LENGTH: 1185
<212> TYPE: DNA
<213> ORGANISM: Clostridium thermocellum
<220> FEATURE:
<221> NAME/KEY: CDS
<222> LOCATION: (1)..(1185)
<223> OTHER INFORMATION: ferrulic acid esterase of CtXynZ

<400> SEQUENCE: 3

-continued

| | | |
|---|---|---|
| atg gcc gcc tcc ctc ccg acc atg ccg ccg tcc ggc tac gac cag gtg<br>Met Ala Ala Ser Leu Pro Thr Met Pro Pro Ser Gly Tyr Asp Gln Val<br>1               5                   10                  15 | 48 |
| cgc aac ggc gtg ccg cgc ggc cag gtg gtg aac atc tcc tac ttc tcc<br>Arg Asn Gly Val Pro Arg Gly Gln Val Val Asn Ile Ser Tyr Phe Ser<br>            20                  25                  30 | 96 |
| acc gcc acc aac tcc acc cgc ccg gcc cgc gtg tac ctc ccg ccg ggc<br>Thr Ala Thr Asn Ser Thr Arg Pro Ala Arg Val Tyr Leu Pro Pro Gly<br>        35                  40                  45 | 144 |
| tac tcc aag gac aag aag tac tcc gtg ctc tac ctc ctc cac ggc atc<br>Tyr Ser Lys Asp Lys Lys Tyr Ser Val Leu Tyr Leu Leu His Gly Ile<br>    50                  55                  60 | 192 |
| ggc ggc tcc gag aac gac tgg ttc gag ggc ggc ggc cgc gcc aac gtg<br>Gly Gly Ser Glu Asn Asp Trp Phe Glu Gly Gly Gly Arg Ala Asn Val<br>65                  70                  75                  80 | 240 |
| atc gcc gac aac ctc atc gcc gag ggc aag atc aag ccg ctc atc atc<br>Ile Ala Asp Asn Leu Ile Ala Glu Gly Lys Ile Lys Pro Leu Ile Ile<br>                85                  90                  95 | 288 |
| gtg acc ccg aac acc aac gcc gcc ggc ccg ggc atc gcc gac ggc tac<br>Val Thr Pro Asn Thr Asn Ala Ala Gly Pro Gly Ile Ala Asp Gly Tyr<br>            100                 105                 110 | 336 |
| gag aac ttc acc aag gac ctc ctc aac tcc ctc atc ccg tac atc gag<br>Glu Asn Phe Thr Lys Asp Leu Leu Asn Ser Leu Ile Pro Tyr Ile Glu<br>        115                 120                 125 | 384 |
| tcc aac tac tcc gtg tac acc gac cgc gag cac cgc gcc atc gcc ggc<br>Ser Asn Tyr Ser Val Tyr Thr Asp Arg Glu His Arg Ala Ile Ala Gly<br>    130                 135                 140 | 432 |
| ctc tct atg ggc ggc ggc cag tcc ttc aac atc ggc ctc acc aac ctc<br>Leu Ser Met Gly Gly Gly Gln Ser Phe Asn Ile Gly Leu Thr Asn Leu<br>145                 150                 155                 160 | 480 |
| gac aag ttc gcc tac atc ggc ccg atc tcc gcc gcc ccg aac acc tac<br>Asp Lys Phe Ala Tyr Ile Gly Pro Ile Ser Ala Ala Pro Asn Thr Tyr<br>                165                 170                 175 | 528 |
| ccg aac gag cgc ctc ttc ccg gac ggc ggc aag gcc gcc cgc gag aag<br>Pro Asn Glu Arg Leu Phe Pro Asp Gly Gly Lys Ala Ala Arg Glu Lys<br>            180                 185                 190 | 576 |
| ctc aag ctc ctc ttc atc gcc tgc ggc acc aac gac tcc ctc atc ggc<br>Leu Lys Leu Leu Phe Ile Ala Cys Gly Thr Asn Asp Ser Leu Ile Gly<br>        195                 200                 205 | 624 |
| ttc ggc cag cgc gtg cac gag tac tgc gtg gcc aac aac atc aac cac<br>Phe Gly Gln Arg Val His Glu Tyr Cys Val Ala Asn Asn Ile Asn His<br>    210                 215                 220 | 672 |
| gtg tac tgg ctc atc cag ggc ggc ggc cac gac ttc aac gtg tgg aag<br>Val Tyr Trp Leu Ile Gln Gly Gly Gly His Asp Phe Asn Val Trp Lys<br>225                 230                 235                 240 | 720 |
| ccg ggc ctc tgg aac ttc ctc cag atg gcc gac gag gcc ggc ctc acc<br>Pro Gly Leu Trp Asn Phe Leu Gln Met Ala Asp Glu Ala Gly Leu Thr<br>                245                 250                 255 | 768 |
| cgc gac ggc aac acc ccg gtg ccg acc ccg tcc ccg aag ccg gcc aac<br>Arg Asp Gly Asn Thr Pro Val Pro Thr Pro Ser Pro Lys Pro Ala Asn<br>            260                 265                 270 | 816 |
| acc cgc atc gag gcc gag gac tac gac ggc atc aac tcc tcc tcc atc<br>Thr Arg Ile Glu Ala Glu Asp Tyr Asp Gly Ile Asn Ser Ser Ser Ile<br>        275                 280                 285 | 864 |
| gag atc atc ggc gtg ccg ccg gag ggc ggc cgc ggc atc ggc tac atc<br>Glu Ile Ile Gly Val Pro Pro Glu Gly Gly Arg Gly Ile Gly Tyr Ile<br>    290                 295                 300 | 912 |
| acc tcc ggc gac tac ctc gtg tac aag tcc atc gac ttc ggc aac ggc<br>Thr Ser Gly Asp Tyr Leu Val Tyr Lys Ser Ile Asp Phe Gly Asn Gly<br>305                 310                 315                 320 | 960 |

```
gcc acc tcc ttc aag gcc aag gtg gcc aac gcc aac acc tcc aac atc     1008
Ala Thr Ser Phe Lys Ala Lys Val Ala Asn Ala Asn Thr Ser Asn Ile
            325                 330                 335 gag ctt cgc ctc aac ggc ccg aac ggc acc ctc atc ggc acc ctc tcc     1056
Glu Leu Arg Leu Asn Gly Pro Asn Gly Thr Leu Ile Gly Thr Leu Ser
        340                 345                 350 gtg aag tcc acc ggc gac tgg aac acc tac gag gag cag acc tgc tcc     1104
Val Lys Ser Thr Gly Asp Trp Asn Thr Tyr Glu Glu Gln Thr Cys Ser
    355                 360                 365 atc tcc aag gtg acc ggc atc aac gac ctc tac ctc gtg ttc aag ggc     1152
Ile Ser Lys Val Thr Gly Ile Asn Asp Leu Tyr Leu Val Phe Lys Gly
370                 375                 380 ccg gtg aac atc gac tgg ttc acc ttc ggc gtg                         1185
Pro Val Asn Ile Asp Trp Phe Thr Phe Gly Val
385             390                 395

<210> SEQ ID NO 4
<211> LENGTH: 395
<212> TYPE: PRT
<213> ORGANISM: Clostridium thermocellum

<400> SEQUENCE: 4

Met Ala Ala Ser Leu Pro Thr Met Pro Pro Ser Gly Tyr Asp Gln Val
1               5                   10                  15

Arg Asn Gly Val Pro Arg Gly Gln Val Val Asn Ile Ser Tyr Phe Ser
            20                  25                  30

Thr Ala Thr Asn Ser Thr Arg Pro Ala Arg Val Tyr Leu Pro Pro Gly
        35                  40                  45

Tyr Ser Lys Asp Lys Lys Tyr Ser Val Leu Tyr Leu Leu His Gly Ile
    50                  55                  60

Gly Gly Ser Glu Asn Asp Trp Phe Glu Gly Gly Arg Ala Asn Val
65                  70                  75                  80

Ile Ala Asp Asn Leu Ile Ala Glu Gly Lys Ile Lys Pro Leu Ile Ile
                85                  90                  95

Val Thr Pro Asn Thr Asn Ala Ala Gly Pro Gly Ile Ala Asp Gly Tyr
            100                 105                 110

Glu Asn Phe Thr Lys Asp Leu Leu Asn Ser Leu Ile Pro Tyr Ile Glu
        115                 120                 125

Ser Asn Tyr Ser Val Tyr Thr Asp Arg Glu His Arg Ala Ile Ala Gly
    130                 135                 140

Leu Ser Met Gly Gly Gly Gln Ser Phe Asn Ile Gly Leu Thr Asn Leu
145                 150                 155                 160

Asp Lys Phe Ala Tyr Ile Gly Pro Ile Ser Ala Ala Pro Asn Thr Tyr
                165                 170                 175

Pro Asn Glu Arg Leu Phe Pro Asp Gly Lys Ala Ala Arg Glu Lys
            180                 185                 190

Leu Lys Leu Leu Phe Ile Ala Cys Gly Thr Asn Asp Ser Leu Ile Gly
        195                 200                 205

Phe Gly Gln Arg Val His Glu Tyr Cys Val Ala Asn Ile Asn His
    210                 215                 220

Val Tyr Trp Leu Ile Gln Gly Gly His Asp Phe Asn Val Trp Lys
225                 230                 235                 240

Pro Gly Leu Trp Asn Phe Leu Gln Met Ala Asp Glu Ala Gly Leu Thr
                245                 250                 255

Arg Asp Gly Asn Thr Pro Val Pro Thr Pro Ser Pro Lys Pro Ala Asn
            260                 265                 270
```

```
Thr Arg Ile Glu Ala Glu Asp Tyr Asp Gly Ile Asn Ser Ser Ile
        275                 280                 285
Glu Ile Ile Gly Val Pro Pro Glu Gly Arg Gly Ile Gly Tyr Ile
    290                 295                 300
Thr Ser Gly Asp Tyr Leu Val Tyr Lys Ser Ile Asp Phe Gly Asn Gly
305                 310                 315                 320
Ala Thr Ser Phe Lys Ala Lys Val Ala Asn Ala Asn Thr Ser Asn Ile
                325                 330                 335
Glu Leu Arg Leu Asn Gly Pro Asn Gly Thr Leu Ile Gly Thr Leu Ser
            340                 345                 350
Val Lys Ser Thr Gly Asp Trp Asn Thr Tyr Glu Gln Thr Cys Ser
        355                 360                 365
Ile Ser Lys Val Thr Gly Ile Asn Asp Leu Tyr Leu Val Phe Lys Gly
    370                 375                 380
Pro Val Asn Ile Asp Trp Phe Thr Phe Gly Val
385                 390                 395
```

<210> SEQ ID NO 5
<211> LENGTH: 3090
<212> TYPE: DNA
<213> ORGANISM: Thermotoga maritima
<220> FEATURE:
<221> NAME/KEY: CDS
<222> LOCATION: (1)..(3090)
<223> OTHER INFORMATION: XynA from T. maritima

<400> SEQUENCE: 5

```
atg gca agc ggt gtt ctg agc ttt ggt aaa gaa gca agc agc aaa ggc     48
Met Ala Ser Gly Val Leu Ser Phe Gly Lys Glu Ala Ser Ser Lys Gly
1               5                   10                  15 gat agc agc ctg gaa acc gtt ctg gca ctg agc ttt gaa ggc acc acc     96
Asp Ser Ser Leu Glu Thr Val Leu Ala Leu Ser Phe Glu Gly Thr Thr
            20                  25                  30 gaa ggt gtt gtt ccg ttt ggt aaa gat gtt gtt ctg acc gca agc cag    144
Glu Gly Val Val Pro Phe Gly Lys Asp Val Val Leu Thr Ala Ser Gln
        35                  40                  45 gat gtt gca gca gat ggt gaa tat agc ctg aaa gtg gaa aat cgt acc    192
Asp Val Ala Ala Asp Gly Glu Tyr Ser Leu Lys Val Glu Asn Arg Thr
    50                  55                  60 agc ccg tgg gat ggt gtt gaa att gat ctg acc ggc aaa gtt aaa agc    240
Ser Pro Trp Asp Gly Val Glu Ile Asp Leu Thr Gly Lys Val Lys Ser
65                  70                  75                  80 ggt gca gat tat ctg ctg tcc ttt cag gtt tat cag agc agt gat gca    288
Gly Ala Asp Tyr Leu Leu Ser Phe Gln Val Tyr Gln Ser Ser Asp Ala
                85                  90                  95 ccg cag ctg ttt aat gtt gtt gca cgc acc gaa gat gaa aaa ggt gaa    336
Pro Gln Leu Phe Asn Val Val Ala Arg Thr Glu Asp Glu Lys Gly Glu
            100                 105                 110 cgc tat gat gtg atc ctg gat aaa gtt gtt gtt agc gac cac tgg aaa    384
Arg Tyr Asp Val Ile Leu Asp Lys Val Val Val Ser Asp His Trp Lys
        115                 120                 125 gaa att ctg gtt ccg ttt agc ccg acc ttt gaa ggt aca ccg gca aaa    432
Glu Ile Leu Val Pro Phe Ser Pro Thr Phe Glu Gly Thr Pro Ala Lys
    130                 135                 140 tac agc ctg att atc gtg gca agc aaa aac acc aac ttt aat ttt tat    480
Tyr Ser Leu Ile Ile Val Ala Ser Lys Asn Thr Asn Phe Asn Phe Tyr
145                 150                 155                 160
```

```
ctg gat aaa gtc cag gtt ctg gca ccg aaa gaa tct ggt ccg aaa gtg      528
Leu Asp Lys Val Gln Val Leu Ala Pro Lys Glu Ser Gly Pro Lys Val
            165                 170                 175 att tat gaa acc agc ttt gaa aat ggt gtt ggt gat tgg cag cct cgt      576
Ile Tyr Glu Thr Ser Phe Glu Asn Gly Val Gly Asp Trp Gln Pro Arg
        180                 185                 190 ggt gat gtt aat att gaa gcc agc agc gaa gtt gca cat agc ggt aaa      624
Gly Asp Val Asn Ile Glu Ala Ser Ser Glu Val Ala His Ser Gly Lys
    195                 200                 205 agc agc ctg ttt att agc aat cgt cag aaa ggt tgg cag ggt gca cag      672
Ser Ser Leu Phe Ile Ser Asn Arg Gln Lys Gly Trp Gln Gly Ala Gln
210                 215                 220 atc aat ctg aaa ggc att ctg aaa acc ggt aaa acc tat gca ttt gag      720
Ile Asn Leu Lys Gly Ile Leu Lys Thr Gly Lys Thr Tyr Ala Phe Glu
225                 230                 235                 240 gca tgg gtt tat cag aat agc ggt cag gat cag acc att att atg acc      768
Ala Trp Val Tyr Gln Asn Ser Gly Gln Asp Gln Thr Ile Ile Met Thr
            245                 250                 255 atg cag cgc aaa tat agc tct gat gca agc acc cag tat gaa tgg att      816
Met Gln Arg Lys Tyr Ser Ser Asp Ala Ser Thr Gln Tyr Glu Trp Ile
        260                 265                 270 aaa agc gca acc gtt ccg agc ggt cag tgg gtt cag ctg tct ggc acc      864
Lys Ser Ala Thr Val Pro Ser Gly Gln Trp Val Gln Leu Ser Gly Thr
    275                 280                 285 tat acc att ccg gca ggc gtt acc gtt gaa gat ctg acc ctg tat ttc      912
Tyr Thr Ile Pro Ala Gly Val Thr Val Glu Asp Leu Thr Leu Tyr Phe
290                 295                 300 gaa agc cag aat ccg acc ctg gaa ttt tat gtg gac gac gtg aaa att      960
Glu Ser Gln Asn Pro Thr Leu Glu Phe Tyr Val Asp Asp Val Lys Ile
305                 310                 315                 320 gtt gat acc acc tct gcc gaa atc aaa att gag atg gaa ccg gaa aaa     1008
Val Asp Thr Thr Ser Ala Glu Ile Lys Ile Glu Met Glu Pro Glu Lys
            325                 330                 335 gaa att ccg gca ctg aaa gaa gtg ctg aaa gat tac ttt aaa gtt ggt     1056
Glu Ile Pro Ala Leu Lys Glu Val Leu Lys Asp Tyr Phe Lys Val Gly
        340                 345                 350 gtt gca ctg ccg agc aaa gtt ttt ctg aac ccg aaa gat att gag ctg     1104
Val Ala Leu Pro Ser Lys Val Phe Leu Asn Pro Lys Asp Ile Glu Leu
    355                 360                 365 att acg aaa cac ttt aac agc atc acc gca gaa aat gaa atg aaa ccg     1152
Ile Thr Lys His Phe Asn Ser Ile Thr Ala Glu Asn Glu Met Lys Pro
370                 375                 380 gaa agc ctg ctg gca ggc att gaa aat ggc aaa ctg aaa ttc cgt ttc     1200
Glu Ser Leu Leu Ala Gly Ile Glu Asn Gly Lys Leu Lys Phe Arg Phe
385                 390                 395                 400 gaa acc gca gat aaa tat atc cag ttt gtg gaa gaa aat ggc atg gtt     1248
Glu Thr Ala Asp Lys Tyr Ile Gln Phe Val Glu Glu Asn Gly Met Val
            405                 410                 415 att cgt ggt cat acc ctg gtt tgg cat aat cag aca ccg gat tgg ttt     1296
Ile Arg Gly His Thr Leu Val Trp His Asn Gln Thr Pro Asp Trp Phe
        420                 425                 430 ttc aaa gat gag aac ggc aat ctg ctg tct aaa gaa gca atg acc gaa     1344
Phe Lys Asp Glu Asn Gly Asn Leu Leu Ser Lys Glu Ala Met Thr Glu
    435                 440                 445 cgc ctg aaa gaa tat atc cat acc gtg gtg ggc cat ttt aaa ggt aaa     1392
Arg Leu Lys Glu Tyr Ile His Thr Val Val Gly His Phe Lys Gly Lys
450                 455                 460 gtg tat gcc tgg gat gtt gtt aat gaa gcc gtt gat ccg aat cag ccg     1440
Val Tyr Ala Trp Asp Val Val Asn Glu Ala Val Asp Pro Asn Gln Pro
465                 470                 475                 480
```

-continued

| | |
|---|---|
| gat ggt ctg cgt cgt agc acc tgg tat cag att atg ggt ccg gat tat<br>Asp Gly Leu Arg Arg Ser Thr Trp Tyr Gln Ile Met Gly Pro Asp Tyr<br>                485                            490                      495 | 1488 |
| att gaa ctg gcc ttt aaa ttt gca cgt gaa gca gat ccg gat gcc aaa<br>Ile Glu Leu Ala Phe Lys Phe Ala Arg Glu Ala Asp Pro Asp Ala Lys<br>                500                            505                      510 | 1536 |
| ctg ttt tac aac gat tat aac acc ttt gaa cct cgc aaa cgc gat att<br>Leu Phe Tyr Asn Asp Tyr Asn Thr Phe Glu Pro Arg Lys Arg Asp Ile<br>                515                            520                      525 | 1584 |
| atc tat aat ctg gtg aaa gat ctg aaa gaa aaa ggc ctg att gat ggt<br>Ile Tyr Asn Leu Val Lys Asp Leu Lys Glu Lys Gly Leu Ile Asp Gly<br>        530                            535                            540 | 1632 |
| att ggt atg cag tgt cat att agc ctg gcc acc gat att aaa caa atc<br>Ile Gly Met Gln Cys His Ile Ser Leu Ala Thr Asp Ile Lys Gln Ile<br>545                            550                            555                      560 | 1680 |
| gaa gaa gcc att aaa aaa ttc agc acc att ccg ggt att gaa atc cat<br>Glu Glu Ala Ile Lys Lys Phe Ser Thr Ile Pro Gly Ile Glu Ile His<br>                      565                            570                      575 | 1728 |
| atc acc gaa ctg gat atg agc gtt tat cgt gat agc agc agc aat tat<br>Ile Thr Glu Leu Asp Met Ser Val Tyr Arg Asp Ser Ser Ser Asn Tyr<br>                580                            585                      590 | 1776 |
| ccg gaa gca ccg cgt acc gca ctg att gaa cag gca cac aaa atg atg<br>Pro Glu Ala Pro Arg Thr Ala Leu Ile Glu Gln Ala His Lys Met Met<br>                      595                            600                      605 | 1824 |
| cag ctg ttt gaa att ttt aag aag tat agc aac gtc att acg aac gtt<br>Gln Leu Phe Glu Ile Phe Lys Lys Tyr Ser Asn Val Ile Thr Asn Val<br>        610                            615                            620 | 1872 |
| acc ttt tgg ggt ctg aaa gat gac tat agc tgg cgt gca acc cgt cgt<br>Thr Phe Trp Gly Leu Lys Asp Asp Tyr Ser Trp Arg Ala Thr Arg Arg<br>625                            630                            635                      640 | 1920 |
| aat gat tgg cct ctg atc ttc gat aaa gat cat cag gca aaa ctg gca<br>Asn Asp Trp Pro Leu Ile Phe Asp Lys Asp His Gln Ala Lys Leu Ala<br>                645                            650                      655 | 1968 |
| tat tgg gca att gtt gca ccg gaa gtt ctg cct ccg ctg ccg aaa gaa<br>Tyr Trp Ala Ile Val Ala Pro Glu Val Leu Pro Pro Leu Pro Lys Glu<br>                  660                            665                      670 | 2016 |
| tct cgt att agc gaa ggt gaa gca gtt gtt gtt ggc atg atg gat gat<br>Ser Arg Ile Ser Glu Gly Glu Ala Val Val Val Gly Met Met Asp Asp<br>            675                            680                            685 | 2064 |
| agc tac ctg atg tct aaa ccg att gaa atc ctg gat gaa gag ggt aat<br>Ser Tyr Leu Met Ser Lys Pro Ile Glu Ile Leu Asp Glu Glu Gly Asn<br>            690                            695                            700 | 2112 |
| gtt aaa gca acc att cgt gcc gtt tgg aaa gat agc acc atc tat atc<br>Val Lys Ala Thr Ile Arg Ala Val Trp Lys Asp Ser Thr Ile Tyr Ile<br>705                            710                            715                      720 | 2160 |
| tat ggt gag gtg cag gac aaa acc aaa aaa ccg gca gaa gat ggc gtt<br>Tyr Gly Glu Val Gln Asp Lys Thr Lys Lys Pro Ala Glu Asp Gly Val<br>                      725                            730                      735 | 2208 |
| gcc att ttt att aac ccg aac aat gaa cgt acc ccg tat ctg cag ccg<br>Ala Ile Phe Ile Asn Pro Asn Asn Glu Arg Thr Pro Tyr Leu Gln Pro<br>                740                            745                      750 | 2256 |
| gat gat acc tat gca gtt ctg tgg acc aat tgg aaa acc gaa gtg aat<br>Asp Asp Thr Tyr Ala Val Leu Trp Thr Asn Trp Lys Thr Glu Val Asn<br>        755                            760                            765 | 2304 |
| cgt gaa gat gtt cag gtg aaa aaa ttt gtg ggt ccg ggt ttt cgt cgt<br>Arg Glu Asp Val Gln Val Lys Lys Phe Val Gly Pro Gly Phe Arg Arg<br>770                            775                            780 | 2352 |

```
tat agc ttc gaa atg agc att aca att ccg ggt gtg gag ttc aaa aaa    2400
Tyr Ser Phe Glu Met Ser Ile Thr Ile Pro Gly Val Glu Phe Lys Lys
785                 790                 795                 800 gat agc tac atc ggt ttt gat gca gcc gtt atc gat gat ggt aaa tgg    2448
Asp Ser Tyr Ile Gly Phe Asp Ala Ala Val Ile Asp Asp Gly Lys Trp
                805                 810                 815 tat agc tgg tcc gat acc acc aat agc cag aaa acc aac acc atg aat    2496
Tyr Ser Trp Ser Asp Thr Thr Asn Ser Gln Lys Thr Asn Thr Met Asn
            820                 825                 830 tat ggc acc ctg aaa ctg gaa ggt att atg gtt gca acc gcc aaa tat    2544
Tyr Gly Thr Leu Lys Leu Glu Gly Ile Met Val Ala Thr Ala Lys Tyr
        835                 840                 845 ggt aca ccg gtg att gat ggc gaa att gat gaa att tgg aat acc acc    2592
Gly Thr Pro Val Ile Asp Gly Glu Ile Asp Glu Ile Trp Asn Thr Thr
    850                 855                 860 gaa gag att gaa acc aaa gca gtt gca atg ggt agc ctg gat aaa aat    2640
Glu Glu Ile Glu Thr Lys Ala Val Ala Met Gly Ser Leu Asp Lys Asn
865                 870                 875                 880 gcc acc gca aaa gtt cgt gtt ctg tgg gat gag aac tat ctg tat gtt    2688
Ala Thr Ala Lys Val Arg Val Leu Trp Asp Glu Asn Tyr Leu Tyr Val
                885                 890                 895 ctg gcc att gtt aaa gat ccg gtg ctg aac aaa gat aat agc aat ccg    2736
Leu Ala Ile Val Lys Asp Pro Val Leu Asn Lys Asp Asn Ser Asn Pro
            900                 905                 910 tgg gaa cag gat agc gtg gaa atc ttt atc gat gaa aat aat cat aaa    2784
Trp Glu Gln Asp Ser Val Glu Ile Phe Ile Asp Glu Asn Asn His Lys
        915                 920                 925 acc ggc tat tat gaa gat gat gat gcc cag ttt cgc gtg aat tat atg    2832
Thr Gly Tyr Tyr Glu Asp Asp Asp Ala Gln Phe Arg Val Asn Tyr Met
    930                 935                 940 aac gaa cag acc ttt ggc acc ggt ggt tct ccg gca cgt ttt aaa acc    2880
Asn Glu Gln Thr Phe Gly Thr Gly Gly Ser Pro Ala Arg Phe Lys Thr
945                 950                 955                 960 gca gtg aaa ctg att gaa ggt ggc tat att gtt gaa gca gcc att aaa    2928
Ala Val Lys Leu Ile Glu Gly Gly Tyr Ile Val Glu Ala Ala Ile Lys
                965                 970                 975 tgg aaa acc att aaa ccg acc ccg aat acc gtt att ggc ttt aac atc    2976
Trp Lys Thr Ile Lys Pro Thr Pro Asn Thr Val Ile Gly Phe Asn Ile
            980                 985                 990 cag gtg aat gat gcc aat gaa aaa ggt cag cgt gtg ggt att att agc    3024
Gln Val Asn Asp Ala Asn Glu Lys Gly Gln Arg Val Gly Ile Ile Ser
        995                 1000                1005 tgg tct gat ccg aca aat aat tct tgg cgt gac ccg agc aaa ttt        3069
Trp Ser Asp Pro Thr Asn Asn Ser Trp Arg Asp Pro Ser Lys Phe
    1010                1015                1020 ggt aat ctg cgc ctg att aaa                                        3090
Gly Asn Leu Arg Leu Ile Lys
        1025                1030

<210> SEQ ID NO 6
<211> LENGTH: 1030
<212> TYPE: PRT
<213> ORGANISM: Thermotoga maritima

<400> SEQUENCE: 6

Met Ala Ser Gly Val Leu Ser Phe Gly Lys Glu Ala Ser Ser Lys Gly
1               5                   10                  15

Asp Ser Ser Leu Glu Thr Val Leu Ala Leu Ser Phe Glu Gly Thr Thr
            20                  25                  30
```

```
Glu Gly Val Val Pro Phe Gly Lys Asp Val Val Leu Thr Ala Ser Gln
            35                  40                  45

Asp Val Ala Ala Asp Gly Glu Tyr Ser Leu Lys Val Glu Asn Arg Thr
 50                  55                  60

Ser Pro Trp Asp Gly Val Glu Ile Asp Leu Thr Gly Lys Val Lys Ser
 65                  70                  75                  80

Gly Ala Asp Tyr Leu Leu Ser Phe Gln Val Tyr Gln Ser Ser Asp Ala
                85                  90                  95

Pro Gln Leu Phe Asn Val Val Ala Arg Thr Glu Asp Glu Lys Gly Glu
            100                 105                 110

Arg Tyr Asp Val Ile Leu Asp Lys Val Val Ser Asp His Trp Lys
            115                 120                 125

Glu Ile Leu Val Pro Phe Ser Pro Thr Phe Glu Gly Thr Pro Ala Lys
            130                 135                 140

Tyr Ser Leu Ile Ile Val Ala Ser Lys Asn Thr Asn Phe Asn Phe Tyr
145                 150                 155                 160

Leu Asp Lys Val Gln Val Leu Ala Pro Lys Ser Gly Pro Lys Val
            165                 170                 175

Ile Tyr Glu Thr Ser Phe Glu Asn Gly Val Gly Asp Trp Gln Pro Arg
            180                 185                 190

Gly Asp Val Asn Ile Glu Ala Ser Ser Glu Val Ala His Ser Gly Lys
            195                 200                 205

Ser Ser Leu Phe Ile Ser Asn Arg Gln Lys Gly Trp Gln Gly Ala Gln
    210                 215                 220

Ile Asn Leu Lys Gly Ile Leu Lys Thr Gly Lys Thr Tyr Ala Phe Glu
225                 230                 235                 240

Ala Trp Val Tyr Gln Asn Ser Gly Gln Asp Gln Thr Ile Ile Met Thr
                245                 250                 255

Met Gln Arg Lys Tyr Ser Ser Asp Ala Ser Thr Gln Tyr Glu Trp Ile
            260                 265                 270

Lys Ser Ala Thr Val Pro Ser Gly Gln Trp Val Gln Leu Ser Gly Thr
            275                 280                 285

Tyr Thr Ile Pro Ala Gly Val Thr Val Glu Asp Leu Thr Leu Tyr Phe
            290                 295                 300

Glu Ser Gln Asn Pro Thr Leu Glu Phe Tyr Val Asp Asp Val Lys Ile
305                 310                 315                 320

Val Asp Thr Thr Ser Ala Glu Ile Lys Ile Glu Met Glu Pro Glu Lys
            325                 330                 335

Glu Ile Pro Ala Leu Lys Glu Val Leu Lys Asp Tyr Phe Lys Val Gly
            340                 345                 350

Val Ala Leu Pro Ser Lys Val Phe Leu Asn Pro Lys Asp Ile Glu Leu
            355                 360                 365

Ile Thr Lys His Phe Asn Ser Ile Thr Ala Glu Asn Glu Met Lys Pro
            370                 375                 380

Glu Ser Leu Leu Ala Gly Ile Glu Asn Gly Lys Leu Lys Phe Arg Phe
385                 390                 395                 400

Glu Thr Ala Asp Lys Tyr Ile Gln Phe Val Glu Glu Asn Gly Met Val
            405                 410                 415

Ile Arg Gly His Thr Leu Val Trp His Asn Gln Thr Pro Asp Trp Phe
            420                 425                 430

Phe Lys Asp Glu Asn Gly Asn Leu Leu Ser Lys Glu Ala Met Thr Glu
            435                 440                 445
```

-continued

```
Arg Leu Lys Glu Tyr Ile His Thr Val Val Gly His Phe Lys Gly Lys
    450                 455                 460
Val Tyr Ala Trp Asp Val Val Asn Glu Ala Val Asp Pro Asn Gln Pro
465                 470                 475                 480
Asp Gly Leu Arg Arg Ser Thr Trp Tyr Gln Ile Met Gly Pro Asp Tyr
                485                 490                 495
Ile Glu Leu Ala Phe Lys Phe Ala Arg Glu Ala Asp Pro Asp Ala Lys
            500                 505                 510
Leu Phe Tyr Asn Asp Tyr Asn Thr Phe Glu Pro Arg Lys Arg Asp Ile
        515                 520                 525
Ile Tyr Asn Leu Val Lys Asp Leu Lys Glu Lys Gly Leu Ile Asp Gly
    530                 535                 540
Ile Gly Met Gln Cys His Ile Ser Leu Ala Thr Asp Ile Lys Gln Ile
545                 550                 555                 560
Glu Glu Ala Ile Lys Lys Phe Ser Thr Ile Pro Gly Ile Glu Ile His
                565                 570                 575
Ile Thr Glu Leu Asp Met Ser Val Tyr Arg Asp Ser Ser Ser Asn Tyr
            580                 585                 590
Pro Glu Ala Pro Arg Thr Ala Leu Ile Glu Gln Ala His Lys Met Met
        595                 600                 605
Gln Leu Phe Glu Ile Phe Lys Lys Tyr Ser Asn Val Ile Thr Asn Val
    610                 615                 620
Thr Phe Trp Gly Leu Lys Asp Asp Tyr Ser Trp Arg Ala Thr Arg Arg
625                 630                 635                 640
Asn Asp Trp Pro Leu Ile Phe Asp Lys Asp His Gln Ala Lys Leu Ala
                645                 650                 655
Tyr Trp Ala Ile Val Ala Pro Glu Val Leu Pro Leu Pro Lys Glu
            660                 665                 670
Ser Arg Ile Ser Glu Gly Glu Ala Val Val Gly Met Met Asp Asp
        675                 680                 685
Ser Tyr Leu Met Ser Lys Pro Ile Glu Ile Leu Asp Glu Glu Gly Asn
    690                 695                 700
Val Lys Ala Thr Ile Arg Ala Val Trp Lys Asp Ser Thr Ile Tyr Ile
705                 710                 715                 720
Tyr Gly Glu Val Gln Asp Lys Thr Lys Lys Pro Ala Glu Asp Gly Val
                725                 730                 735
Ala Ile Phe Ile Asn Pro Asn Asn Glu Arg Thr Pro Tyr Leu Gln Pro
            740                 745                 750
Asp Asp Thr Tyr Ala Val Leu Trp Thr Asn Trp Lys Thr Glu Val Asn
        755                 760                 765
Arg Glu Asp Val Gln Val Lys Lys Phe Val Gly Pro Gly Phe Arg Arg
    770                 775                 780
Tyr Ser Phe Glu Met Ser Ile Thr Ile Pro Gly Val Glu Phe Lys Lys
785                 790                 795                 800
Asp Ser Tyr Ile Gly Phe Asp Ala Ala Val Ile Asp Asp Gly Lys Trp
                805                 810                 815
Tyr Ser Trp Ser Asp Thr Thr Asn Ser Gln Lys Thr Asn Thr Met Asn
            820                 825                 830
Tyr Gly Thr Leu Lys Leu Glu Gly Ile Met Val Ala Thr Ala Lys Tyr
        835                 840                 845
Gly Thr Pro Val Ile Asp Gly Ile Asp Glu Ile Trp Asn Thr Thr
    850                 855                 860
```

```
Glu Glu Ile Glu Thr Lys Ala Val Ala Met Gly Ser Leu Asp Lys Asn
865                 870                 875                 880

Ala Thr Ala Lys Val Arg Val Leu Trp Asp Glu Asn Tyr Leu Tyr Val
                885                 890                 895

Leu Ala Ile Val Lys Asp Pro Val Leu Asn Lys Asp Asn Ser Asn Pro
            900                 905                 910

Trp Glu Gln Asp Ser Val Glu Ile Phe Ile Asp Glu Asn Asn His Lys
        915                 920                 925

Thr Gly Tyr Tyr Glu Asp Asp Ala Gln Phe Arg Val Asn Tyr Met
    930                 935                 940

Asn Glu Gln Thr Phe Gly Thr Gly Gly Ser Pro Ala Arg Phe Lys Thr
945                 950                 955                 960

Ala Val Lys Leu Ile Glu Gly Gly Tyr Ile Val Glu Ala Ala Ile Lys
                965                 970                 975

Trp Lys Thr Ile Lys Pro Thr Pro Asn Thr Val Ile Gly Phe Asn Ile
            980                 985                 990

Gln Val Asn Asp Ala Asn Glu Lys  Gly Gln Arg Val Gly  Ile Ile Ser
        995                 1000                1005

Trp Ser  Asp Pro Thr Asn Asn  Ser Trp Arg Asp Pro  Ser Lys Phe
    1010                1015                 1020

Gly Asn  Leu Arg Leu Ile Lys
    1025                1030

<210> SEQ ID NO 7
<211> LENGTH: 987
<212> TYPE: DNA
<213> ORGANISM: Thermotoga maritima
<220> FEATURE:
<221> NAME/KEY: CDS
<222> LOCATION: (1)..(987)
<223> OTHER INFORMATION: XynB from T. maritima

<400> SEQUENCE: 7 atg cag aat gta tct ctg aga gaa ctc gca gaa aag ctg aac atc tat      48
Met Gln Asn Val Ser Leu Arg Glu Leu Ala Glu Lys Leu Asn Ile Tyr
1               5                   10                  15 att ggt ttt gcc gca atc aac aac ttt tgg tct ctt tcc gac gca gaa      96
Ile Gly Phe Ala Ala Ile Asn Asn Phe Trp Ser Leu Ser Asp Ala Glu
            20                  25                  30 aag tac atg gaa gtt gca aga aga gaa ttc aac atc ctg acc cct gag     144
Lys Tyr Met Glu Val Ala Arg Arg Glu Phe Asn Ile Leu Thr Pro Glu
        35                  40                  45 aac cag atg aag tgg gat acg att cat cca gaa aga gac aga tac aat     192
Asn Gln Met Lys Trp Asp Thr Ile His Pro Glu Arg Asp Arg Tyr Asn
    50                  55                  60 ttc act ccc gct gaa aaa cac gtt gag ttt gca gaa gaa aac gac atg     240
Phe Thr Pro Ala Glu Lys His Val Glu Phe Ala Glu Glu Asn Asp Met
65                  70                  75                  80 atc gtg cat gga cac act ctt gtc tgg cac aac cag ctt cct gga tgg     288
Ile Val His Gly His Thr Leu Val Trp His Asn Gln Leu Pro Gly Trp
                85                  90                  95 atc act ggt aga gaa tgg aca aag gaa gaa ctt ttg aac gtt ctt gaa     336
Ile Thr Gly Arg Glu Trp Thr Lys Glu Glu Leu Leu Asn Val Leu Glu
            100                 105                 110 gac cac ata aaa acg gtg gtg tct cat ttc aaa ggt aga gtg aag atc     384
Asp His Ile Lys Thr Val Val Ser His Phe Lys Gly Arg Val Lys Ile
        115                 120                 125
```

| | | |
|---|---|---|
| tgg gat gtg gtg aac gaa gcg gtg agc gat tct gga acc tac agg gaa<br>Trp Asp Val Val Asn Glu Ala Val Ser Asp Ser Gly Thr Tyr Arg Glu<br>130                     135                     140 | | 432 |
| agc gtg tgg tac aag acg atc ggt cct gaa tac att gaa aaa gcg ttc<br>Ser Val Trp Tyr Lys Thr Ile Gly Pro Glu Tyr Ile Glu Lys Ala Phe<br>145                     150                     155                     160 | | 480 |
| aga tgg gca aaa gaa gcc gat cca gat gcg att ctc atc tac aac gac<br>Arg Trp Ala Lys Glu Ala Asp Pro Asp Ala Ile Leu Ile Tyr Asn Asp<br>                 165                     170                     175 | | 528 |
| tac agc ata gaa gaa atc aac gca aaa tcg aac ttc gtc tac aac atg<br>Tyr Ser Ile Glu Glu Ile Asn Ala Lys Ser Asn Phe Val Tyr Asn Met<br>180                     185                     190 | | 576 |
| ata aaa gag ctg aaa gaa aag gga gta cct gtt gat gga ata gga ttt<br>Ile Lys Glu Leu Lys Glu Lys Gly Val Pro Val Asp Gly Ile Gly Phe<br>                 195                     200                     205 | | 624 |
| cag atg cac ata gac tac aga ggg ctc aat tat gac agt ttc aga agg<br>Gln Met His Ile Asp Tyr Arg Gly Leu Asn Tyr Asp Ser Phe Arg Arg<br>210                     215                     220 | | 672 |
| aat ttg gag aga ttt gcg aaa ctc ggt ctt caa ata tac atc aca gag<br>Asn Leu Glu Arg Phe Ala Lys Leu Gly Leu Gln Ile Tyr Ile Thr Glu<br>225                     230                     235                     240 | | 720 |
| atg gat gtg aga att cct ctc agt ggt tcg gag gag tat tat ttg aaa<br>Met Asp Val Arg Ile Pro Leu Ser Gly Ser Glu Glu Tyr Tyr Leu Lys<br>                 245                     250                     255 | | 768 |
| aaa cag gct gaa gtt tgt gcg aag atc ttc gat ata tgc ttg gac aac<br>Lys Gln Ala Glu Val Cys Ala Lys Ile Phe Asp Ile Cys Leu Asp Asn<br>                 260                     265                     270 | | 816 |
| cct gca gtt aaa gcg atc cag ttt tgg gga ttc aca gac aaa tac tcc<br>Pro Ala Val Lys Ala Ile Gln Phe Trp Gly Phe Thr Asp Lys Tyr Ser<br>275                     280                     285 | | 864 |
| tgg gtt ccc ggc ttt ttc aaa ggg tac ggg aaa gcg ttg ctc ttc gat<br>Trp Val Pro Gly Phe Phe Lys Gly Tyr Gly Lys Ala Leu Leu Phe Asp<br>290                     295                     300 | | 912 |
| gag aat tac aac ccc aag cct tgt tat tac gcg ata aaa gag gtg ctg<br>Glu Asn Tyr Asn Pro Lys Pro Cys Tyr Tyr Ala Ile Lys Glu Val Leu<br>305                     310                     315                     320 | | 960 |
| gag aaa aag ata gaa gaa aga aaa tga<br>Glu Lys Lys Ile Glu Glu Arg Lys<br>                 325 | | 987 |

<210> SEQ ID NO 8
<211> LENGTH: 328
<212> TYPE: PRT
<213> ORGANISM: Thermotoga maritima

<400> SEQUENCE: 8

Met Gln Asn Val Ser Leu Arg Glu Leu Ala Glu Lys Leu Asn Ile Tyr
1                  5                        10                   15

Ile Gly Phe Ala Ala Ile Asn Asn Phe Trp Ser Leu Ser Asp Ala Glu
                 20                        25                        30

Lys Tyr Met Glu Val Ala Arg Arg Glu Phe Asn Ile Leu Thr Pro Glu
                 35                        40                        45

Asn Gln Met Lys Trp Asp Thr Ile His Pro Glu Arg Asp Arg Tyr Asn
        50                        55                        60

Phe Thr Pro Ala Glu Lys His Val Glu Phe Ala Glu Glu Asn Asp Met
65                  70                        75                   80

Ile Val His Gly His Thr Leu Val Trp His Asn Gln Leu Pro Gly Trp
                 85                        90                        95

```
Ile Thr Gly Arg Glu Trp Thr Lys Glu Leu Leu Asn Val Leu Glu
            100                 105                 110

Asp His Ile Lys Thr Val Val Ser His Phe Lys Gly Arg Val Lys Ile
        115                 120                 125

Trp Asp Val Val Asn Glu Ala Val Ser Asp Ser Gly Thr Tyr Arg Glu
    130                 135                 140

Ser Val Trp Tyr Lys Thr Ile Gly Pro Glu Tyr Ile Glu Lys Ala Phe
145                 150                 155                 160

Arg Trp Ala Lys Glu Ala Asp Pro Asp Ala Ile Leu Ile Tyr Asn Asp
                165                 170                 175

Tyr Ser Ile Glu Glu Ile Asn Ala Lys Ser Asn Phe Val Tyr Asn Met
            180                 185                 190

Ile Lys Glu Leu Lys Glu Lys Gly Val Pro Val Asp Gly Ile Gly Phe
        195                 200                 205

Gln Met His Ile Asp Tyr Arg Gly Leu Asn Tyr Asp Ser Phe Arg Arg
    210                 215                 220

Asn Leu Glu Arg Phe Ala Lys Leu Gly Leu Gln Ile Tyr Ile Thr Glu
225                 230                 235                 240

Met Asp Val Arg Ile Pro Leu Ser Gly Ser Glu Glu Tyr Tyr Leu Lys
                245                 250                 255

Lys Gln Ala Glu Val Cys Ala Lys Ile Phe Asp Ile Cys Leu Asp Asn
            260                 265                 270

Pro Ala Val Lys Ala Ile Gln Phe Trp Gly Phe Thr Asp Lys Tyr Ser
        275                 280                 285

Trp Val Pro Gly Phe Phe Lys Gly Tyr Gly Lys Ala Leu Leu Phe Asp
    290                 295                 300

Glu Asn Tyr Asn Pro Lys Pro Cys Tyr Tyr Ala Ile Lys Glu Val Leu
305                 310                 315                 320

Glu Lys Lys Ile Glu Glu Arg Lys
                325

<210> SEQ ID NO 9
<211> LENGTH: 1143
<212> TYPE: DNA
<213> ORGANISM: Bacillus stearothermophilus
<220> FEATURE:
<221> NAME/KEY: CDS
<222> LOCATION: (1)..(1143)
<223> OTHER INFORMATION: XynA from Bacillus

<400> SEQUENCE: 9 atg aaa aat gcc gat agc tat gcc aaa aaa ccg cat att agc gca ctg       48
Met Lys Asn Ala Asp Ser Tyr Ala Lys Lys Pro His Ile Ser Ala Leu
1               5                   10                  15 aat gca ccg cag ctg gat cag cgt tat aaa aat gaa ttt acc att ggt       96
Asn Ala Pro Gln Leu Asp Gln Arg Tyr Lys Asn Glu Phe Thr Ile Gly
            20                  25                  30 gca gca gtt gaa ccg tat cag ctg cag aat gaa aaa gat gtg cag atg       144
Ala Ala Val Glu Pro Tyr Gln Leu Gln Asn Glu Lys Asp Val Gln Met
        35                  40                  45 ctg aaa cgc cac ttt aat agc att gtg gcc gaa aat gtg atg aaa ccg       192
Leu Lys Arg His Phe Asn Ser Ile Val Ala Glu Asn Val Met Lys Pro
    50                  55                  60 att agc att cag ccg gaa gaa ggc aaa ttt aat ttt gaa cag gcc gat       240
Ile Ser Ile Gln Pro Glu Glu Gly Lys Phe Asn Phe Glu Gln Ala Asp
65                  70                  75                  80
```

```
cgc att gtt aaa ttt gcc aaa gcc aat ggt atg gat att cgc ttt cat        288
Arg Ile Val Lys Phe Ala Lys Ala Asn Gly Met Asp Ile Arg Phe His
            85                  90                  95 acc ctg gtt tgg cat agc cag gtt ccg cag tgg ttt ttt ctg gat aaa        336
Thr Leu Val Trp His Ser Gln Val Pro Gln Trp Phe Phe Leu Asp Lys
        100                 105                 110 gaa ggc aaa ccg atg gtt aat gaa acc gat ccg gtt aaa cgc gaa cag        384
Glu Gly Lys Pro Met Val Asn Glu Thr Asp Pro Val Lys Arg Glu Gln
    115                 120                 125 aat aaa cag ctg ctg ctg aaa cgt ctg gaa acc cat att aaa acc att        432
Asn Lys Gln Leu Leu Leu Lys Arg Leu Glu Thr His Ile Lys Thr Ile
130                 135                 140 gtg gaa cgc tat aaa gat gac att aaa tat tgg gat gtg gtg aat gaa        480
Val Glu Arg Tyr Lys Asp Asp Ile Lys Tyr Trp Asp Val Val Asn Glu
145                 150                 155                 160 gtt gtt ggt gat gat ggt aaa ctg cgt aat agc ccg tgg tat cag att        528
Val Val Gly Asp Asp Gly Lys Leu Arg Asn Ser Pro Trp Tyr Gln Ile
                165                 170                 175 gca ggc att gat tat att aaa gtg gcc ttt cag gca gca cgt aaa tat        576
Ala Gly Ile Asp Tyr Ile Lys Val Ala Phe Gln Ala Ala Arg Lys Tyr
            180                 185                 190 ggt ggc gat aat att aaa ctg tat atg aat gat tat aat acc gaa gtg        624
Gly Gly Asp Asn Ile Lys Leu Tyr Met Asn Asp Tyr Asn Thr Glu Val
        195                 200                 205 gaa ccg aaa cgt acc gca ctg tat aat ctg gtg aaa cag ctg aaa gaa        672
Glu Pro Lys Arg Thr Ala Leu Tyr Asn Leu Val Lys Gln Leu Lys Glu
    210                 215                 220 gaa ggc gtt ccg att gac ggt att ggt cat cag agc cat att cag att        720
Glu Gly Val Pro Ile Asp Gly Ile Gly His Gln Ser His Ile Gln Ile
225                 230                 235                 240 ggt tgg ccg agc gaa gca gaa att gaa aaa acc att aat atg ttt gca        768
Gly Trp Pro Ser Glu Ala Glu Ile Glu Lys Thr Ile Asn Met Phe Ala
                245                 250                 255 gca ctg ggt ctg gat aat cag att acc gaa ctg gat gtt agc atg tat        816
Ala Leu Gly Leu Asp Asn Gln Ile Thr Glu Leu Asp Val Ser Met Tyr
            260                 265                 270 ggt tgg cct ccg cgt gca tat ccg acc tat gat gca att ccg aaa cag        864
Gly Trp Pro Pro Arg Ala Tyr Pro Thr Tyr Asp Ala Ile Pro Lys Gln
        275                 280                 285 aaa ttt ctg gat cag gca gcc cgt tat gat cgt ctg ttt aaa ctg tat        912
Lys Phe Leu Asp Gln Ala Ala Arg Tyr Asp Arg Leu Phe Lys Leu Tyr
    290                 295                 300 gaa aaa ctg agc gat aaa att agc aat gtg acc ttt tgg ggt att gca        960
Glu Lys Leu Ser Asp Lys Ile Ser Asn Val Thr Phe Trp Gly Ile Ala
305                 310                 315                 320 gat aat cat acc tgg ctg gat agc cgt gca gat gtt tat tat gat gcc       1008
Asp Asn His Thr Trp Leu Asp Ser Arg Ala Asp Val Tyr Tyr Asp Ala
                325                 330                 335 aat ggc aat gtt gtt gtt gat ccg aat gca ccg tat gcc aaa gtg gaa       1056
Asn Gly Asn Val Val Val Asp Pro Asn Ala Pro Tyr Ala Lys Val Glu
            340                 345                 350 aaa ggc aaa ggt aaa gat gca ccg ttt gtt ttt ggt ccg gat tat aaa       1104
Lys Gly Lys Gly Lys Asp Ala Pro Phe Val Phe Gly Pro Asp Tyr Lys
        355                 360                 365 gtg aaa ccg gca tat tgg gcc att att gat cat aaa tga                   1143
Val Lys Pro Ala Tyr Trp Ala Ile Ile Asp His Lys
    370                 375                 380

<210> SEQ ID NO 10
<211> LENGTH: 380
```

<212> TYPE: PRT
<213> ORGANISM: Bacillus stearothermophilus

<400> SEQUENCE: 10

Met Lys Asn Ala Asp Ser Tyr Ala Lys Lys Pro His Ile Ser Ala Leu
1               5                   10                  15

Asn Ala Pro Gln Leu Asp Gln Arg Tyr Lys Asn Glu Phe Thr Ile Gly
            20                  25                  30

Ala Ala Val Glu Pro Tyr Gln Leu Gln Asn Glu Lys Asp Val Gln Met
        35                  40                  45

Leu Lys Arg His Phe Asn Ser Ile Val Ala Glu Asn Val Met Lys Pro
    50                  55                  60

Ile Ser Ile Gln Pro Glu Glu Gly Lys Phe Asn Phe Glu Gln Ala Asp
65                  70                  75                  80

Arg Ile Val Lys Phe Ala Lys Ala Asn Gly Met Asp Ile Arg Phe His
                85                  90                  95

Thr Leu Val Trp His Ser Gln Val Pro Gln Trp Phe Phe Leu Asp Lys
            100                 105                 110

Glu Gly Lys Pro Met Val Asn Glu Thr Asp Pro Val Lys Arg Glu Gln
        115                 120                 125

Asn Lys Gln Leu Leu Leu Lys Arg Leu Glu Thr His Ile Lys Thr Ile
    130                 135                 140

Val Glu Arg Tyr Lys Asp Asp Ile Lys Tyr Trp Asp Val Val Asn Glu
145                 150                 155                 160

Val Val Gly Asp Asp Gly Lys Leu Arg Asn Ser Pro Trp Tyr Gln Ile
                165                 170                 175

Ala Gly Ile Asp Tyr Ile Lys Val Ala Phe Gln Ala Ala Arg Lys Tyr
            180                 185                 190

Gly Gly Asp Asn Ile Lys Leu Tyr Met Asn Asp Tyr Asn Thr Glu Val
        195                 200                 205

Glu Pro Lys Arg Thr Ala Leu Tyr Asn Leu Val Lys Gln Leu Lys Glu
    210                 215                 220

Glu Gly Val Pro Ile Asp Gly Ile Gly His Gln Ser His Ile Gln Ile
225                 230                 235                 240

Gly Trp Pro Ser Glu Ala Glu Ile Glu Lys Thr Ile Asn Met Phe Ala
                245                 250                 255

Ala Leu Gly Leu Asp Asn Gln Ile Thr Glu Leu Asp Val Ser Met Tyr
            260                 265                 270

Gly Trp Pro Pro Arg Ala Tyr Pro Thr Tyr Asp Ala Ile Pro Lys Gln
        275                 280                 285

Lys Phe Leu Asp Gln Ala Ala Arg Tyr Asp Arg Leu Phe Lys Leu Tyr
    290                 295                 300

Glu Lys Leu Ser Asp Lys Ile Ser Asn Val Thr Phe Trp Gly Ile Ala
305                 310                 315                 320

Asp Asn His Thr Trp Leu Asp Ser Arg Ala Asp Val Tyr Tyr Asp Ala
                325                 330                 335

Asn Gly Asn Val Val Asp Pro Asn Ala Pro Tyr Ala Lys Val Glu
            340                 345                 350

Lys Gly Lys Gly Lys Asp Ala Pro Phe Val Phe Gly Pro Asp Tyr Lys
        355                 360                 365

Val Lys Pro Ala Tyr Trp Ala Ile Ile Asp His Lys
    370                 375                 380

<210> SEQ ID NO 11

<211> LENGTH: 999
<212> TYPE: DNA
<213> ORGANISM: Dictyoglomus thermophilum
<220> FEATURE:
<221> NAME/KEY: CDS
<222> LOCATION: (1)..(999)
<223> OTHER INFORMATION: XynA from Dt

<400> SEQUENCE: 11

| | | | | | | | | | | | | | | | | |
|---|---|---|---|---|---|---|---|---|---|---|---|---|---|---|---|---|
| atg | ttt | ctg | aaa | gaa | gaa | gcc | aaa | ggt | atg | gaa | att | ccg | agc | ctg | aaa | 48 |
| Met | Phe | Leu | Lys | Glu | Glu | Ala | Lys | Gly | Met | Glu | Ile | Pro | Ser | Leu | Lys | |
| 1 | | | | 5 | | | | | 10 | | | | | 15 | | |
| gaa | gtg | tat | aaa | gat | tac | ttt | acc | atc | ggt | gca | gca | gtt | agc | cat | ctg | 96 |
| Glu | Val | Tyr | Lys | Asp | Tyr | Phe | Thr | Ile | Gly | Ala | Ala | Val | Ser | His | Leu | |
| | | | 20 | | | | | 25 | | | | | 30 | | | |
| aat | att | tat | cat | tat | gag | aac | ctg | ctg | aaa | aaa | cat | ttt | aat | agc | ctg | 144 |
| Asn | Ile | Tyr | His | Tyr | Glu | Asn | Leu | Leu | Lys | Lys | His | Phe | Asn | Ser | Leu | |
| | | 35 | | | | | 40 | | | | | 45 | | | | |
| aca | ccg | gaa | aat | cag | atg | aaa | tgg | gaa | gtg | att | cat | ccg | aaa | ccg | tat | 192 |
| Thr | Pro | Glu | Asn | Gln | Met | Lys | Trp | Glu | Val | Ile | His | Pro | Lys | Pro | Tyr | |
| | 50 | | | | | 55 | | | | | 60 | | | | | |
| gtg | tat | gat | ttt | ggt | ccg | gca | gat | gaa | att | gtt | gat | ttt | gcc | atg | aaa | 240 |
| Val | Tyr | Asp | Phe | Gly | Pro | Ala | Asp | Glu | Ile | Val | Asp | Phe | Ala | Met | Lys | |
| 65 | | | | | 70 | | | | | 75 | | | | | 80 | |
| aat | ggc | atg | aaa | gtt | cgt | ggt | cat | acc | ctg | gtt | tgg | cat | aat | cag | aca | 288 |
| Asn | Gly | Met | Lys | Val | Arg | Gly | His | Thr | Leu | Val | Trp | His | Asn | Gln | Thr | |
| | | | | 85 | | | | | 90 | | | | | 95 | | |
| ccg | ggt | tgg | gtt | tat | gca | ggc | acc | aaa | gat | gaa | att | ctg | gca | cgc | ctg | 336 |
| Pro | Gly | Trp | Val | Tyr | Ala | Gly | Thr | Lys | Asp | Glu | Ile | Leu | Ala | Arg | Leu | |
| | | | 100 | | | | | 105 | | | | | 110 | | | |
| aaa | gaa | cat | att | aaa | gaa | gtg | gtg | ggc | cat | tat | aaa | ggt | aaa | gtg | tat | 384 |
| Lys | Glu | His | Ile | Lys | Glu | Val | Val | Gly | His | Tyr | Lys | Gly | Lys | Val | Tyr | |
| | | 115 | | | | | 120 | | | | | 125 | | | | |
| gcc | tgg | gat | gtt | gtt | aat | gaa | gcc | ctg | agc | gat | aat | ccg | aat | gaa | ttt | 432 |
| Ala | Trp | Asp | Val | Val | Asn | Glu | Ala | Leu | Ser | Asp | Asn | Pro | Asn | Glu | Phe | |
| | 130 | | | | | 135 | | | | | 140 | | | | | |
| ctg | cgt | cgt | gca | ccg | tgg | tat | gat | att | tgt | ggc | gaa | gaa | gtg | att | gaa | 480 |
| Leu | Arg | Arg | Ala | Pro | Trp | Tyr | Asp | Ile | Cys | Gly | Glu | Glu | Val | Ile | Glu | |
| 145 | | | | | 150 | | | | | 155 | | | | | 160 | |
| aaa | gcc | ttt | att | tgg | gca | cat | gaa | gtt | gat | ccg | gat | gcc | aaa | ctg | ttt | 528 |
| Lys | Ala | Phe | Ile | Trp | Ala | His | Glu | Val | Asp | Pro | Asp | Ala | Lys | Leu | Phe | |
| | | | | 165 | | | | | 170 | | | | | 175 | | |
| tat | aat | gat | tat | aat | ctg | gaa | gat | ccg | att | aaa | cgc | gaa | aaa | gcc | tat | 576 |
| Tyr | Asn | Asp | Tyr | Asn | Leu | Glu | Asp | Pro | Ile | Lys | Arg | Glu | Lys | Ala | Tyr | |
| | | | 180 | | | | | 185 | | | | | 190 | | | |
| aaa | ctg | gtg | aaa | aaa | ctg | aaa | gat | aaa | ggc | gtt | ccg | att | cat | ggt | att | 624 |
| Lys | Leu | Val | Lys | Lys | Leu | Lys | Asp | Lys | Gly | Val | Pro | Ile | His | Gly | Ile | |
| | | 195 | | | | | 200 | | | | | 205 | | | | |
| ggt | att | cag | ggt | cat | tgg | acc | ctg | gca | tgg | ccg | acc | ccg | aaa | atg | ctg | 672 |
| Gly | Ile | Gln | Gly | His | Trp | Thr | Leu | Ala | Trp | Pro | Thr | Pro | Lys | Met | Leu | |
| | 210 | | | | | 215 | | | | | 220 | | | | | |
| gaa | gat | agc | att | aaa | cgt | ttt | gcc | gaa | ctg | ggt | gtt | gaa | gtt | cag | gtg | 720 |
| Glu | Asp | Ser | Ile | Lys | Arg | Phe | Ala | Glu | Leu | Gly | Val | Glu | Val | Gln | Val | |
| 225 | | | | | 230 | | | | | 235 | | | | | 240 | |
| acc | gag | ttc | gac | atc | agc | atc | tac | tat | gat | cgc | aat | gaa | aac | aat | aac | 768 |
| Thr | Glu | Phe | Asp | Ile | Ser | Ile | Tyr | Tyr | Asp | Arg | Asn | Glu | Asn | Asn | Asn | |
| | | | | 245 | | | | | 250 | | | | | 255 | | |
| ttt | aaa | gtg | cct | ccg | gaa | gat | cgt | ctg | gaa | cgt | cag | gca | cag | ctg | tat | 816 |
| Phe | Lys | Val | Pro | Pro | Glu | Asp | Arg | Leu | Glu | Arg | Gln | Ala | Gln | Leu | Tyr | |
| | | | 260 | | | | | 265 | | | | | 270 | | | |

| | | | | | | | | | | | | | | | |
|---|---|---|---|---|---|---|---|---|---|---|---|---|---|---|---|
| aaa | gaa | gcc | ttt | gaa | att | ctg | cgc | aaa | tac | aaa | ggc | atc | gtg | acc | ggc |
| Lys | Glu | Ala | Phe | Glu | Ile | Leu | Arg | Lys | Tyr | Lys | Gly | Ile | Val | Thr | Gly |
| | | 275 | | | | 280 | | | | | 285 | | | | |

864

| gtg | acc | ttt | tgg | ggt | gtt | gca | gat | gat | tat | acc | tgg | ctg | tat | ttt | tgg |
|---|---|---|---|---|---|---|---|---|---|---|---|---|---|---|---|
| Val | Thr | Phe | Trp | Gly | Val | Ala | Asp | Asp | Tyr | Thr | Trp | Leu | Tyr | Phe | Trp |
| | 290 | | | | | 295 | | | | | 300 | | | | |

912

| ccg | gtt | cgt | ggt | cgt | gaa | gat | tat | ccg | ctg | ctg | ttt | gat | aaa | aat | cat |
|---|---|---|---|---|---|---|---|---|---|---|---|---|---|---|---|
| Pro | Val | Arg | Gly | Arg | Glu | Asp | Tyr | Pro | Leu | Leu | Phe | Asp | Lys | Asn | His |
| 305 | | | | 310 | | | | | 315 | | | | | | 320 |

960

| aat | ccg | aaa | aaa | gcc | ttt | tgg | gaa | att | gtg | aaa | ttt | taa | | | |
|---|---|---|---|---|---|---|---|---|---|---|---|---|---|---|---|
| Asn | Pro | Lys | Lys | Ala | Phe | Trp | Glu | Ile | Val | Lys | Phe | | | | |
| | | | | 325 | | | | | 330 | | | | | | |

999

<210> SEQ ID NO 12
<211> LENGTH: 332
<212> TYPE: PRT
<213> ORGANISM: Dictyoglomus thermophilum

<400> SEQUENCE: 12

Met Phe Leu Lys Glu Glu Ala Lys Gly Met Glu Ile Pro Ser Leu Lys
1               5                   10                  15

Glu Val Tyr Lys Asp Tyr Phe Thr Ile Gly Ala Ala Val Ser His Leu
            20                  25                  30

Asn Ile Tyr His Tyr Glu Asn Leu Leu Lys Lys His Phe Asn Ser Leu
        35                  40                  45

Thr Pro Glu Asn Gln Met Lys Trp Glu Val Ile His Pro Lys Pro Tyr
    50                  55                  60

Val Tyr Asp Phe Gly Pro Ala Asp Glu Ile Val Asp Phe Ala Met Lys
65                  70                  75                  80

Asn Gly Met Lys Val Arg Gly His Thr Leu Val Trp His Asn Gln Thr
                85                  90                  95

Pro Gly Trp Val Tyr Ala Gly Thr Lys Asp Glu Ile Leu Ala Arg Leu
            100                 105                 110

Lys Glu His Ile Lys Glu Val Val Gly His Tyr Lys Gly Lys Val Tyr
        115                 120                 125

Ala Trp Asp Val Val Asn Glu Ala Leu Ser Asp Asn Pro Asn Glu Phe
    130                 135                 140

Leu Arg Arg Ala Pro Trp Tyr Asp Ile Cys Gly Glu Glu Val Ile Glu
145                 150                 155                 160

Lys Ala Phe Ile Trp Ala His Glu Val Asp Pro Asp Ala Lys Leu Phe
                165                 170                 175

Tyr Asn Asp Tyr Asn Leu Glu Asp Pro Ile Lys Arg Glu Lys Ala Tyr
            180                 185                 190

Lys Leu Val Lys Lys Leu Lys Asp Lys Gly Val Pro Ile His Gly Ile
        195                 200                 205

Gly Ile Gln Gly His Trp Thr Leu Ala Trp Pro Thr Pro Lys Met Leu
    210                 215                 220

Glu Asp Ser Ile Lys Arg Phe Ala Glu Leu Gly Val Glu Val Gln Val
225                 230                 235                 240

Thr Glu Phe Asp Ile Ser Ile Tyr Tyr Asp Arg Asn Glu Asn Asn
                245                 250                 255

Phe Lys Val Pro Pro Glu Asp Arg Leu Glu Arg Gln Ala Gln Leu Tyr
            260                 265                 270

Lys Glu Ala Phe Glu Ile Leu Arg Lys Tyr Lys Gly Ile Val Thr Gly
        275                 280                 285

-continued

```
Val Thr Phe Trp Gly Val Ala Asp Asp Tyr Thr Trp Leu Tyr Phe Trp
    290                 295                 300

Pro Val Arg Gly Arg Glu Asp Tyr Pro Leu Leu Phe Asp Lys Asn His
305                 310                 315                 320

Asn Pro Lys Lys Ala Phe Trp Glu Ile Val Lys Phe
                325                 330
```